US008642012B2

(12) United States Patent
Scharschmidt

(10) Patent No.: US 8,642,012 B2
(45) Date of Patent: Feb. 4, 2014

(54) METHODS OF TREATMENT USING AMMONIA-SCAVENGING DRUGS

(75) Inventor: Bruce Scharschmidt, South San Francisco, CA (US)

(73) Assignee: Hyperion Therapeutics, Inc., South San Francisco, CA (US)

( * ) Notice: Subject to any disclaimer, the term of this patent is extended or adjusted under 35 U.S.C. 154(b) by 623 days.

(21) Appl. No.: 12/350,111

(22) Filed: Jan. 7, 2009

(65) Prior Publication Data
US 2010/0008859 A1 Jan. 14, 2010

Related U.S. Application Data

(60) Provisional application No. 61/093,234, filed on Aug. 29, 2008.

(51) Int. Cl.
*A61K 49/00* (2006.01)
(52) U.S. Cl.
USPC .............. 424/9.2; 514/568; 514/432; 514/433
(58) Field of Classification Search
USPC ........................................................ 424/9.2
See application file for complete search history.

(56) References Cited

U.S. PATENT DOCUMENTS

| | | | |
|---|---|---|---|
| 4,284,647 A | 8/1981 | Brusilow et al. | |
| 5,968,979 A | 10/1999 | Brusilow | |
| 6,060,510 A | 5/2000 | Brusilow | |
| 6,083,984 A * | 7/2000 | Brusilow | 514/533 |
| 6,219,567 B1 | 4/2001 | Eggers et al. | |
| 2004/0229948 A1 | 11/2004 | Summar et al. | |
| 2006/0135612 A1 | 6/2006 | Ferrante | |
| 2008/0119554 A1 | 5/2008 | Jalan et al. | |
| 2010/0008859 A1 | 1/2010 | Scharschmidt | |

FOREIGN PATENT DOCUMENTS

| | | |
|---|---|---|
| WO | WO-2005/053607 | 6/2005 |
| WO | WO-2006/056794 | 6/2006 |
| WO | WO-2009/087474 | 7/2009 |
| WO | WO-2009/134460 A1 | 11/2009 |
| WO | WO-2010/250303 A1 | 3/2010 |

OTHER PUBLICATIONS

Berry et al., J Pediatrics (2001) 138:S56-S61.
Brusilow, Pediatric Research (1991) 29:147-150.
Brusilow, Progress in Liver Diseases (1995) 12:293-309.
Brusilow and Finkelstein, J Metabolism (1993) 42:1336-1339.
Chang et al., PNAS USA (2001) 98(17):9808-9813.
FDA Label for Buphenyl, 6 pages.
Kasumov et al., Drug Metabolism and Disposition (2004) 32(1):10-19.
Rudman et al., J Clin Invest (1973) 52:2241-2249.
Singh, Suppl to J Pediatrics (2001) 138(1):S1-55.
Thibault et al., Cancer (1995) 75(12):2932-2938.
Thibault et al., Cancer Research (1994) 54(7):1690-1694.
International Search Report and Written Opinion for PCT/US09/30362, mailed Mar. 2, 2009, 8 pages.
ClinicalTrials.Gov/Archive View of NCT00551200 on Dec. 11, 2007 "Dose-Escalation Safety Study of Glyceryl Tri (4-Phenylbutyrate)(GT4P) to Treat Urea Cycle Disorders" [accessed Oct. 5, 2009], 4 pages.
Comte et al., Journal of Mass Spectrometry (2002) 37(6):581-590.
Lee et al., Journal of Inherited Metabolic Disease (2008) 31(1):91.
Search and Examination Report for British Patent Application No. GB 0915545.8, dated Oct. 8, 2009, 5 pages.
MacArthur et al. (2004). Molecular Genetics and Metabolism 81(1):S67-S73.
Simmell et al. (1986). Pediatric Research 20(11):1117-1121.
Tanner et al. (2007). Journal of Inherited Metabolic Disease 30(5):716-721.
International Search Report and Written Opinion for PCT/US2009/055256, mailed Dec. 30, 2009, 13 pages.
Ambrose, A.M. et al. (1933)."Further Studies on the Detoxification of Phenylacetic Acid.," *J. Biol. Chem.* 101:669-675.
Batshaw M.L. et al. (Dec. 1980). "Treatment of Hyperammonemic Coma Caused by Inborn Errors of Urea Synthesis," *J. Pediatr.* 97(6):893-900.
Batshaw, M.L. et al. (Aug. 1981). "New Approaches to the Diagnosis and Treatment of Inborn Errors of Urea Synthesis," *Pediatrics* 68(2):290-297.
Batshaw M.L. et al. (Jun. 10, 1982). "Treatment of Inborn Errors of Urea Synthesis: Activation of Alternative Pathways of Waste Nitrogen Synthesis and Excretion," *N. Engl. J. Med.* 306(23):1387-1392.
Batshaw, M.L. (1984). "Hyperammonemia," in *Current Problems in Pediatrics*, Lockhart, J.D. ed.: Year Book Medical Publishers, pp. 2-69.
Brusilow, S.W. et al. (Sep. 1, 1979). "New Pathways of Nitrogen Excretion in Inborn Errors of Urea Synthesis," *Lancet* 2(8140):452-454.
Brusilow, S. et al. (Feb. 8, 1980). "Amino Acid Acylation: A Mechanism of Nitrogen Excretion in Inborn Errors of Urea Synthesis," *Science* 207:659-661.
Brusilow, S.W. (Jun. 21, 1984). "Treatment of Episodic Hyperammonemia in Children With Inborn Errors of Urea Synthesis," *N. Engl. J. Med.* 310(25):1630-1634.
Brusilow, S.W. et al. (1991). "Treatment of Urea Cycle Disorders," Chapter 5 in *Treatment of Genetic Diseases*, Desnik, R.J. et al. eds, Churchill Livingstone, New York, New York, pp. 79-94.

(Continued)

*Primary Examiner* — Jon P Weber
*Assistant Examiner* — Tiffany Gough
(74) *Attorney, Agent, or Firm* — Perkins Coie LLP; Patrick Morris

(57) ABSTRACT

The invention provides a method for determining a dose and schedule and making dose adjustments of PBA prodrugs used to treat nitrogen retention states, or ammonia accumulation disorders, by measuring urinary excretion of phenylacetylglutamine and/or total urinary nitrogen. The invention provides methods to select an appropriate dosage of a PBA prodrug based on the patient's dietary protein intake, or based on previous treatments administered to the patient. The methods are applicable to selecting or modifying a dosing regimen for a subject receiving an orally administered ammonia scavenging drug.

12 Claims, 15 Drawing Sheets

(56) References Cited

OTHER PUBLICATIONS

Brusilow, S.W. (Amendment Dated Jul. 25, 1994). "Protocols for Management of Intercurrent Hyperammonemia in Patients with Urea Cycle Disorders," FDA Application to Market a New Drug for Human Use or an Antibiotic Drug for Human Use, Fourteen pages.

Brusilow, S.W. et al. (1995). "Urea Cycle Enzymes," Chapter 32 in *The Metabolic and Molecular bases of Inherited Diseases*, Scriver, C.R. et al. eds., McGraw-Hill, Inc. New York, New York, pp. 1187-1232.

Brusilow, S.W., et al. (1996). "Urea Cycle Disorders: Diagnosis, Pathophysiology, and Therapy," *Adv. Pediatr.* 43:127-170.

Calloway, D.H. et al. (1971). "Sweat and Miscellaneous Nitrogen Losses in Human Balance Studies," *J. Nutrition* 101:775-786.

Calloway, D.H. et al. (1971). "Variation in Endogenous Nitrogen Excretion and Dietary Nitrogen Utilization as Determinants of Human Protein Requirements," *J. Nutrition* 101:205-216.

Camacho, L.H. et al. (2007, e-pub. Oct. 20, 2006). "Phase I Dose Escalation Clinical Trial of Phenylbutyrate Sodium Administered Twice Daily to Patients With Advanced Solid Tumors," *Invest. New Drugs* 25:131-138.

Combined Search and Examination Report mailed on Sep. 9, 2010, for Great Britian Patent Application No. 1013468.2, filed on Aug. 27, 2009, six pages.

Combined Search and Examination Report mailed on Oct. 9, 2009, for Great Britain Patent Application No. GB0915545.8, filed on Aug. 27, 2009, eight pages.

Deferrari, G. et al. (1981). "Brain Metabolism of Amino Acids and Ammonia in Patients with Chronic Renal Insufficiency," *Kidney International* 20;505-510.

Examination Report mailed on Oct. 27, 2010, for United Kingdom Patent Application No. GB0915545.8, filed on Aug. 27, 2009, two pages.

Examination Report mailed Feb. 5, 2010, for United Kingdom Patent Application No. GB0915545.8, filed on Aug. 27, 2009, two page.

Examination Report mailed May 11, 2010, for United Kingdom Patent Application No. GB0915545.8, filed on Aug. 27, 2009, one page.

FDA. (Aug. 2003). "Buphenyl® (Sodium Phenylbutyrate) Label" nine pages.

Gargosky, S. (2006). "High Ammonia Levels Are Associated With Increased Mortality and Coma," Ucyclyd Pharma, Inc., one page.

Gargosky, S. et al. (Oct. 14, 2005). "Results of a Twenty-two Year Clinical Trial: Actue, Adjunctive Pharmacological Treatment of Hyperammonemic Episodes in Patients with Deficiencies in Enzymes of the Urea Cycle," poster, Ucyclyd Pharma, Inc., one page.

Gargosky, S. (Aug. 2, 2005). "Improved Survival of Neonates Following Administration of Ammonul® (Sodium Phenylacetate & Sodium Benzoate) 10% / 10% Injection," SSIEM Poster, six pages.

Gropman, A.L. et al. (Sep.-Oct. 2008, e-pub. Jul. 26, 2008). "$^1$H MRS Identifies Symptomatic and Asymptomatic Subjects With Partial Ornithine Transcarbamylase Deficiency," *Mol. Genet. Metab.* 95(1-2):21-30.

Hyperion Therapeutics. (Mar. 30, 2009). "Hyperion Therapeutics Announces Results for Phase II Study in Urea Cycle Disorders," located at <http://www.hyperiontx.com/press/release/pr_1238518388,> last visited on Apr. 27, 2011, three pages.

Hyperion Therapeutics. (Jun. 2, 2009.) "Hyperion Therapeutics Announces Results of Phase I Study in Patients with Liver Cirrhosis" located at <http://www.hyperiontx.com/press/release/pr_1243891161>, last visited on Apr. 27, 2011, three pages.

International Preliminary Report on Patentability mailed on Mar. 1, 2011, for PCT Application No. PCT/US2009/030362, filed on Jan. 7, 2009, seven pages.

International Preliminary Report on Patentability mailed on Mar. 1, 2011, for PCT Application No. PCT/US2009/055256, filed on Aug. 27, 2009, six pages.

James, M.O. et al. (1972). "The Conjugation of Phenylacetic Acid in Man, Sub-Human Primates and Some Other Non-Primates Species," *Proc. R. Soc. London* 182:25-35.

John, B.A. et al. (Mar. 2009). "The Disposition of HPN-100, A Novel Pharmaceutical Under Development for Potential Treatment of Hyperammonemia, in Cynomologus Monkeys," abstract presented at *ACMG 2009*, one page.

John, B.A. et al. (Mar. 2009). "The Disposition of HPN-100, A Novel Pharmaceutical Under Development for Potential Treatment of Hyperammonemia, in Cynomolgus Monkeys," ACMG 2009 ADME, poster, two pages.

Lee, B. et al. (Aug. 2009). "Dosing and Therapeutic Monitoring of Ammonia Scavenging Drugs and Urinary Phenylacetylglutamine (PAGN) as a Biomarker; Lessons From a Phase 2 Comparison of a Novel Ammonia Scavenging Agent With Sodium Phenylbutyrate (NaPBA)," abstract presented at *ICIEM 2009*, San Diego, CA, one page.

Lee, B. et al. (Aug. 2009). "Dosing and Therapeutic Monitoring of Ammona Scavenging Drugs and Urinary Phenylacetylglutamine (PAGN) as a Biomarker: Lessons From a Phase 2 Comparison of a Novel Ammonia Scavenging Agent with Sodium Phenylbutyrate (NAPBA)," presented at ICIEM 2009, San Diego, CA, poster, one page.

Lee, B. et al. (Mar. 2009). "Phase 2 Study of A Novel Ammonia Scavenging Agent in Adults With Urea Cycle Disorders (UCDs)," abstract presented at *ACMG 2009*, one page.

Lee, B. et al. (Mar. 2009). "Phase 2 Study of A Novel Ammonia Scavenging Agent in Adults with Urea Cycle Disorders (UCDs)," presented at *ACMG 2009*, seventeen pages.

Lee, B. et al. (Aug. 2008). "Preliminary Data on Adult Patients with Urea Cycle Disorders (UCD) in an Open-Label, Switch-Over, Dose-Escalation Study Comparing a New Ammonia Scavenger, Glyceryl Tri (4-Phenylbutyrate) [HPN-100], to Buphenyl® (Sodium Phenylbutyrate [PBA])," abstract presented at *SSIEM 2008*, Lisbon, Portugal, one page.

Lee, B. et al. (Sep. 2008). "Preliminary Data on Adult Patients with Urea Cycle Disorders (UCD) in An Open-Label, Switch-Over, Dose Escalation Study Comparing a New Ammonia Scavenger, Glyceryl Tri (4-Phenylbutyrate) [HPN-100], to Buphenyl® (Sodium Phenylbutyrate [PBA],"presented at *SSIEM 2008*, Lisbon, Portugal, Poster, one page.

Lewis, H.B. (1914). "Studies in the Synthesis of Hippuric Acid in the Animal Organism. II. The Synthesis and Rate of Elimination of Hippuric Acid After Benzoate Ingestion in Man," *J. Biol. Chem.* 18:225-231.

Mansour, A. et al. (Oct. 1997). "Abdominal Operations in Patients with Cirrhosis: Still a Major Surgical Challenge," *Surgery* 122(4):730-735. (Abstract Only.).

Masetri, N.E. et al. (Aug. 1992). "Plasma Glutamine Concentration: A Guide in the Management of Urea Cycle Disorders," *J. Pediatr.* 121(2):259-261.

McGuire, B.M. et al. (2009). "Pharmacokinetic (PK) and Safety Analyses of a Novel Ammonia-Reducing Agent in Healthy Adults and Patients with Cirrhosis," Hyperion Therapeutics, poster, one page.

McGuire, B.M. et al. (May 2009). "Pharmacokinetic (PK) and Safety Analyses of a Novel Ammonia-Reducing Agent in Healthy Adults and Patients with Cirrhosis," abstract presented at *DDW*, May 2009, two pages.

McGuire, B. et al. (Apr. 2008). Pharmacokinetic Safety Study of Sodium Phenylacetate and Sodium Benzoate Administered to Subjects With Hepatic Impairments, *Liver International* 28:743. (Abstract Only).

McGuire, B. et al. (Apr. 2008). "Pharmacokeinetic (PK) Safety Study of Sodium Phenylacetate and Sodium Benzoate Administered to Subjects with Hepatic Impairment," abstract of *The 13$^{th}$ International Symposium*, Abano (Padova), Italy, Apr. 28-May 1, 2008, two pages.

McQuade P.S. (1984). "Analysis and the Effects of Some Drugs on the Metabolism of Phenylethylamine and Phenylacetic Acid," *Neuropsychopharmacol. Biol. Psychiat.* 8:607-614.

Piscitelli, S.C. et al. (1995). "Disposition of Phenylbutyrate and its Metabolites, Phenylacetete and Phenylacetylglutamine," *J. Clin. Pharmacol.* 35:368-373.

(56) References Cited

OTHER PUBLICATIONS

Propst, A. et al. (Aug. 1995). "Prognosis and Life Expectancy in Chronic Liver Disease," *Dig Dis Sci* 40(8):1805-1815. (Abstract Only)

Riley, T.R. et al. (Nov. 15, 2001). "Preventive Strategies in Chronic Liver Disease: Part II. Cirrhosos," *Am. Fam. Physician* 64(10):1735-1740. (Abstract Only).

Shiple, G.J. et al. (1922). "Synthesis of Amino Acids in Animal Organisms. I. Synthesis of Glycocoll and Glutamine in the Human Organism," *J. Am. Chem. Soc.* 44:618-624.

Summar, M.L. et al. (Oct. 2008, e-pub. Jul. 17, 2008). "Diagnosis, Symptoms, Frequency and Mortality of 260 Patients with Urea Cycle Disorders From a 21-Year, Multicentre Study of Acute Hyperammonaemic Episodes," *Acta Paediatr.* 97:1420-1425.

Summar, M. et al. (2007). "Description and Outcomes of 316 Urea Cycle Patients From a 21-Year, Multicenter Study of Acute Hyperammonemic Episodes," Abstract, *presented at Annual Symposium CCH—Congress Centre Hamburg*, Sep. 4-7, 2007, GSSIEM 2007, two pages.

Swedish Orphan International. (Jan. 12, 2007). "Urea Cycle Disorders an International Perspective," Poster, Symposium Swedish Orphan International, Barcelona, Spain, Jan. 12, 2007, one page.

Tuchman, M. et al. (2008, e-pub. Jun. 17, 2008). "Cross-Sectional Multicenter Study of Patients With Urea Cycle Disorders in the United States," *Molec. Genetics Metab.* 94:397-402.

Waterlow, J.C. (Mar. 1963). "The Partition of Nitrogen in the Urine of Malnourished Jamaican Infants," *Am. J. of Clin. Nutrition* 12:235-240.

Zeitlin, P.L. et al. (Jul. 2002). "Evidence of CFTR Function in Cystic Fibrosis After System Administration of 4-Phenylbutyrate," *Mol. Therapy* 6(1):119-126.

Enns, G. M., et al., "Survival After Treatment with Phenylacetate and Benzoate for Urea-Cycle Disorders," N. Eng. J. Med. 356:2282-2292 (2007).

United States Patent and Trademark Office, International Search Report and Written Opinion dated Jun. 4, 2012 for PCT/US2012/028620.

Diaz, G.A., et al., "Phase 3 Blinded, Randomized, Crossover Comparison of Sodium Phenylbutyrate (NaPBA) and Glycerol Phenylbutyrate (GPB): Ammonia (NH3) Control in Adults with Urea Cycle Disorders (UCDs)," Mol. Genet. Metab. 102:276, Society of Inherited Metabolic Disease (SMID) Abstract, (2011).

Ghabril, M., et al., "Glycerol Phenylbutyrate (GPB) Administration in Patients with Cirrhosis and Episodic Hepatic Encephalopathy (HE)," accepted for presentation at Digestive Disease Week, 2012.

Lee, B., et al., "Phase 2 Comparison of a Novel Ammonia Scavenging Agent with Sodium Phenylbutyrate in Patients with Urea Cycle Disorders: Safety, Pharmacokinetics and Ammonia Control," Mol. Genet. Metab. 100:221-228 (2010).

Lichter-Konecki, U., et al., "Ammonia Control in Children with Urea Cycle Disorders (UCDs); Phase 2 Comparison of Sodium Phenylbutyrate and Glycerol Phenylbutyrate," Mol. Genet. Metab. 103:323-329 (2011).

McGuire, B. M., et al., "Pharmacology and Safety of Glycerol Phenylbutyrate in Healthy Adults and Adults with Cirrhosis," Hepatology 51:2077-2085 (2010).

\* cited by examiner

A conventional clinical pharmacology model in which only drug reaching the central (systemic) circulation is assumed to be active.

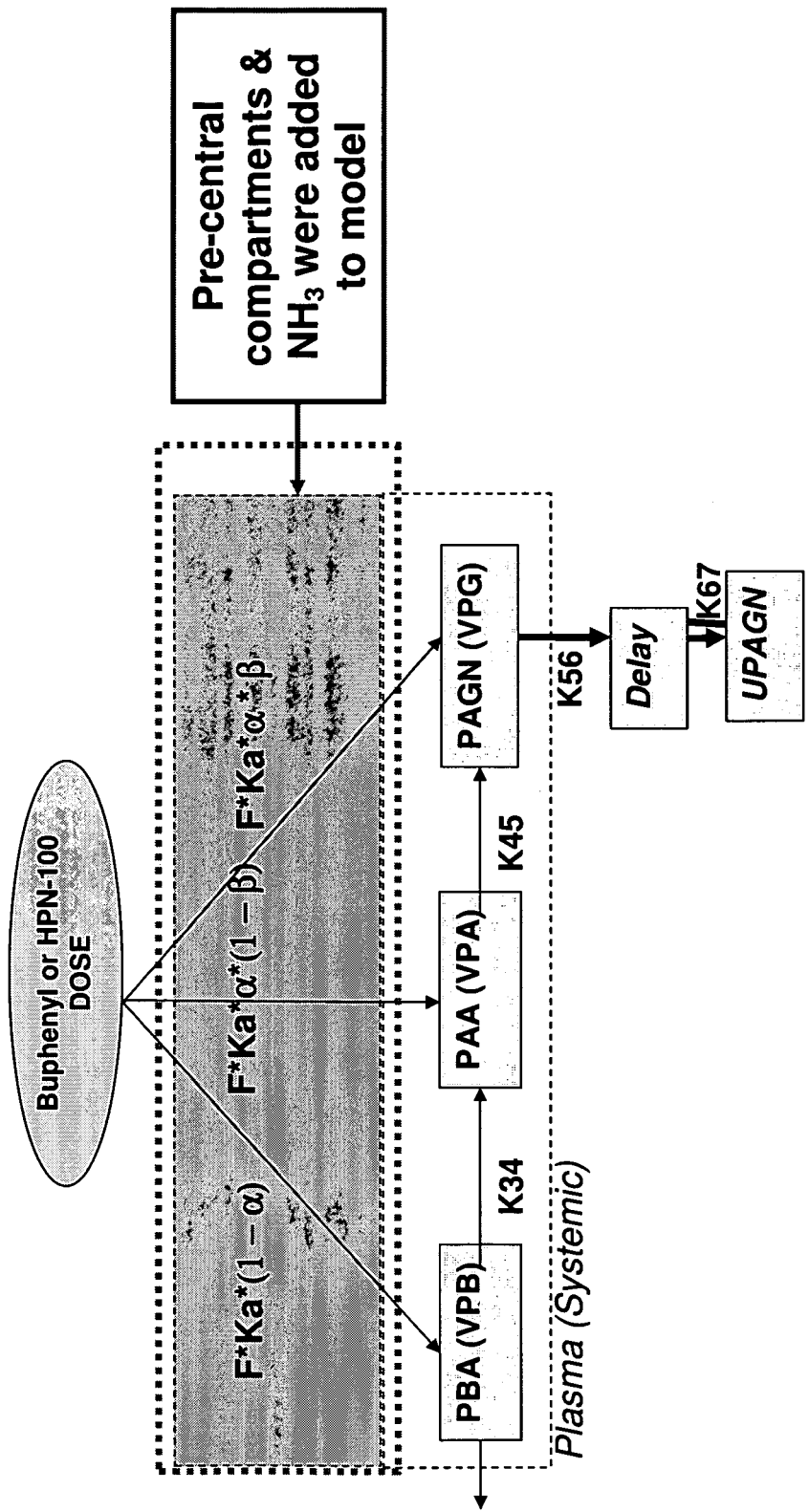

Figure 3

A modified clinical pharmacology model as described in this application in which an ammonia scavenging agent converted into PAGN prior to reaching the systemic circulation is fully active with respect to excretion of waste nitrogen. As a corollary, concentrations of metabolites in the systemic circulation do not correlate consistently with drug effect.

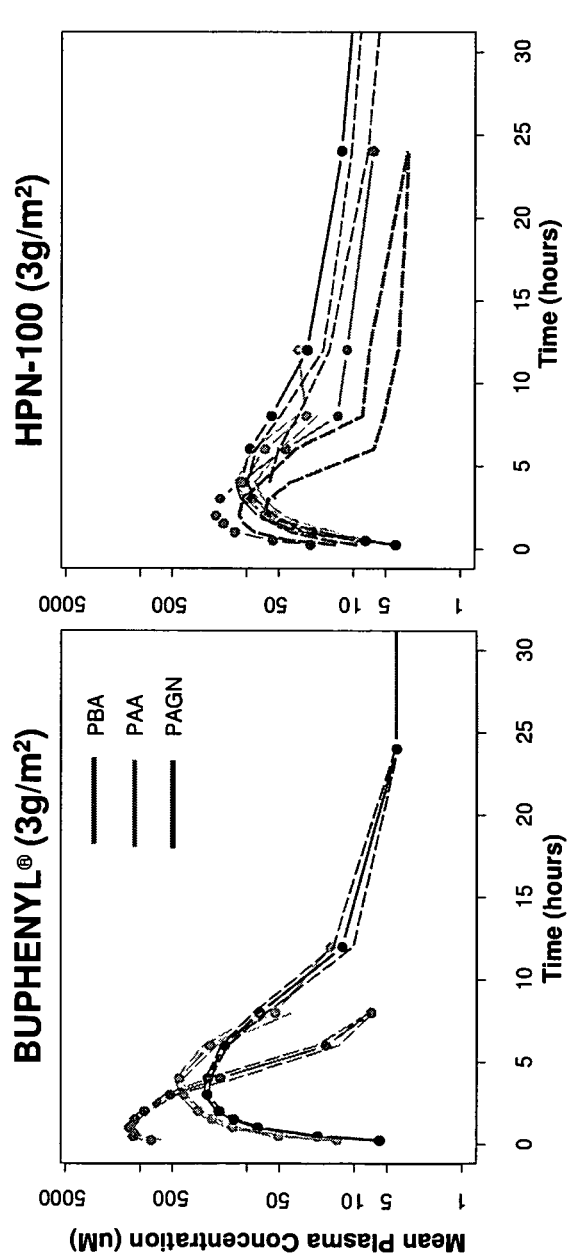

FIGURE 4

In each panel, the curves represent measured levels of PBA, PAA or PAGN in subjects receiving BUPHENYL® (sodium phenylbutyrate) (sodium PBA) at 3g/m² dosage, or HPN-100 in an amount calculated to provide an equimolar amount of PBA to that provided by the sodium PBA dosage. Three curves for each material are for three subjects who received the specified dosages of sodium PBA or HPN-100. In the left panel, the upper curve represents PBA levels; the intermediate one represents PAA levels; and the lowest of the three sets of lines represents PAGN levels. In the right panel, the three lowest curves at the 10-15 hour time span are all for PBA; and the highest three curves at 15-25 hours represent PAGN levels. PAA levels were not determined after approximately 12 hours, and fall generally close to the PAGN curves up to that time.

Relationship between blood ammonia levels (partial time-normalized area under the curve [partial AUC]) and urinary output of PAGN in 10 subjects during steady state treatment with HPN-100 or sodium PBA. Partial AUCs are plotted against the corresponding time of the urine collection, which ranged from 6 to 12 hours.

Schematic anatomic depiction of the systemic and presystemic (represented by the portal vein) compartments. Unlike the case for most drugs which need to pass through the liver to the systemic circulation to exert an effect, PAA converted to PAGN prior to reaching the systemic circulation (e.g. in the liver) is still effective in clearing ammonia from the body.

Figure 9a
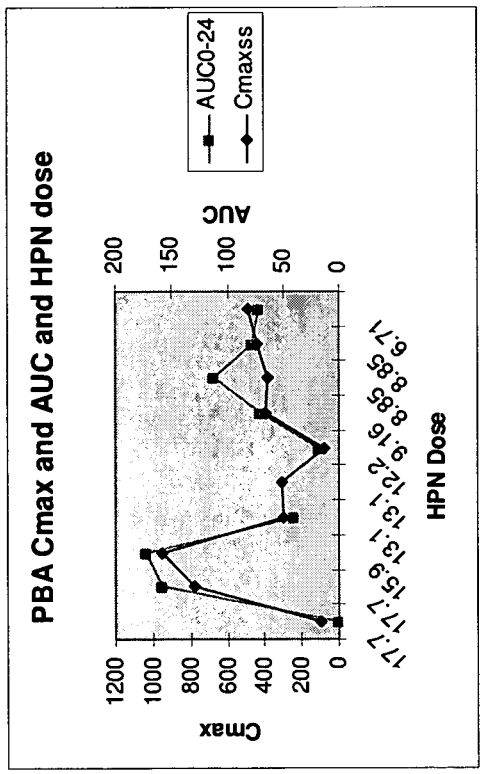
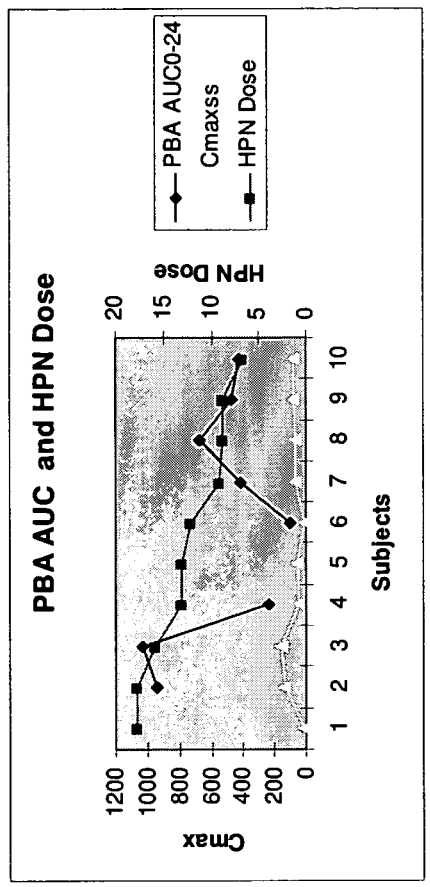
Figure 9 depicts the lack of correlation between drug dose and plasma PBA (9a) and plasma PAA (9b), as compared with a significant correlation with urinary output of PAGN (9c).

Plasma ammonia levels (time-normalized area under the curve [TN-AUC or AUC]) during the day and night in 10 UCD patients treated for seven days with either sodium PBA (BUP) or a PBA equimolar dose of HPN-10.

Plasma ammonia levels (time-normalized area under the curve [TN-AUC]) in 10 UCD patients treated for seven days with sodium PBA (BUP) followed by seven days with a PBA equimolar dose of HPN-100.

Mean plasma ammonia levels (time-normalized area under the curve [TN-AUC]) in 10 UCD patients treated for seven days with sodium PBA followed by seven days with a PBA equimolar dose of HPN-100.

METHODS OF TREATMENT USING AMMONIA-SCAVENGING DRUGS

CROSS-REFERENCE TO RELATED APPLICATIONS

This application claims benefit of priority to U.S. Provisional application Ser. No. 61/093,234, filed Aug. 29, 2008, which is incorporated herein by reference in its entirety. This application is also related to the U.S. provisional patent application entitled "Treating special populations having liver disease with nitrogen-scavenging compounds," naming Sharron Gargosky as inventor, Ser. No. 61/048,830, filed on Apr. 29, 2008.

TECHNICAL FIELD

This invention relates to treatment of patients with nitrogen retention states, in particular urea cycle disorders (UCDs) and cirrhosis complicated by hepatic encephalopathy (HE), using administered compounds that assist in elimination of waste nitrogen from the body. The compounds can be orally administered small-molecule drugs, and the invention provides methods for delivering these compounds and selecting suitable dosages for a patient.

BACKGROUND ART

Drug dosing is usually based upon measurement of blood levels of the active drug species in conjunction with clinical assessment of treatment response. However, the present invention is based on evidence that for certain prodrugs of phenylacetic acid (PAA), measuring the blood level of the prodrug (e.g. PBA) or of PAA formed from it is unreliable. In addition, assessment of treatment effect by measuring levels of ammonia in the blood is inconvenient, because it requires withdrawing multiple blood samples under carefully controlled conditions. Because blood ammonia levels are affected by various factors including dietary protein, they also fail to provide a direct measure of how much ammonia the drug is mobilizing for elimination. The invention demonstrates that prodrugs of phenylbutyric acid (PBA) behave similarly to sodium PBA, in that measuring PBA levels is unreliable for assessing their effectiveness. This invention provides a novel method for dosing in patients with nitrogen retention states, in particular patients with liver disease and clinical manifestations of hepatic encephalopathy and patients with UCDs. It is particularly applicable to prodrugs that liberate or are metabolized to form phenylacetic acid, i.e., prodrugs of PAA, and those prodrugs that are metabolized to form PBA.

Hepatic encephalopathy refers to a spectrum of neurologic signs and symptoms which frequently occur in patients with cirrhosis or certain other types of liver disease.

Urea cycle disorders comprise several inherited deficiencies of enzymes or transporters necessary for the synthesis of urea from ammonia. The urea cycle is depicted in FIG. 1, which also illustrates how certain ammonia-scavenging drugs act to assist in elimination of excessive ammonia. The enzymes including their Enzyme Commission (EC) numbers and modes of inheritance include the following:

Carbamyl phosphate synthetase (CPS; EC Number 6.3.4.16; autosomal recessive),
ornithine transcarbamylase (OTC; EC Number 2.1.3.3; X-linked),
argininosuccinate synthetase (ASS; EC Number 6.3.4.5; autosomal recessive),
argininosuccinate lyase (ASL; EC Number 4.3.2.1; autosomal recessive),
arginase (ARG; EC Number 3.5.3.1; autosomal recessive), and
N-acetyl glutamine synthetase (NAGS 1; EC Number 2.3.1.1; autosomal recessive)

Mitochondrial transporter deficiency states which mimic many features of urea cycle enzyme deficiencies include the following:

Ornithine translocase deficiency (hyperomithinemia, hyperammonemia, homocitrullinuria or HHH Syndrome)
Citrin (aspartate glutamate transporter) deficiency The common feature of UCD and hepatic encephalopathy that render them treatable by methods of the invention is an accumulation of excess waste nitrogen in the body, and hyperammonemia. In normal individuals, the body's intrinsic capacity for waste nitrogen excretion is greater than the body's waste nitrogen production, so waste nitrogen does not accumulate and ammonia does not build up to harmful levels. For patients with nitrogen retention states such as UCD or HE, the body's intrinsic capacity for waste nitrogen excretion is less than the body's waste nitrogen production based on a normal diet that contains significant amounts of protein. As a result, nitrogen builds up in the body of a patient having a nitrogen retention disorder, and usually results in excess ammonia in the blood. This has various toxic effects; drugs that help eliminate the excess ammonia are an important part of an overall management strategy for such disorders.

To avoid build-up of ammonia to toxic levels in patients with nitrogen retention states, dietary intake of protein (a primary source of exogenous waste nitrogen) must be balanced by the patient's ability to eliminate excess ammonia. Dietary protein can be limited, but a healthy diet requires a significant amount of protein, particularly for growing children; thus in addition to controlling dietary protein intake, drugs that assist with elimination of nitrogen are used to reduce ammonia build-up (hyperammonemia). The capacity to eliminate excess ammonia in treated patients can be considered the sum of the patient's endogenous capacity for nitrogen elimination (if any) plus the amount of additional nitrogen-elimination capacity that is provided by a nitrogen scavenging drug. The methods of the invention use a variety of different drugs that reduce excess waste nitrogen and ammonia by converting it to readily-excreted forms, such as phenylacetyl glutamine (PAGN). In some embodiments, the invention relates to methods for determining or adjusting a dosage of an oral drug that forms PAA in vivo, which is converted into PAGN, which is then excreted in urine and thus helps eliminate excess nitrogen.

Based on prior studies in individual UCD patients (e.g. Brusilow, *Pediatric Research*, vol. 29, 147-50 (1991); Brusilow and Finkelstien, *J. Metabolism*, vol. 42, 1336-39 (1993)) in which 80-90% of the nitrogen scavenger sodium phenylbutyrate was reportedly excreted in the urine as PAGN, current treatment guidelines typically either assume complete conversion of sodium phenylbutyrate or other PAA prodrugs to PAGN (e.g. Berry et al., *J. Pediatrics*, vol. 138, S56-S61 (2001)) or do not comment on the implications of incomplete conversion for dosing (e.g. Singh, Urea Cycle Disorders Conference Group '*Consensus Statement from a Conference for the Management of Patients with Urea Cycle Disorders*', Suppl to *J Pediatrics*, vol. 138(1), S1-S5 (2001)).

Current treatment guidelines recommend 4 times per day dosing, based on the fact that PBA is absorbed rapidly from the intestine when administered in the form of sodium PBA and exhibits a short half life in the bloodstream (Urea Cycle Disorders Conference Group 'Consensus Statement' 2001)

Current recommendations for sodium phenylbutyrate dosing indicate that dosage should not exceed 600 mg/kg (for patients weighing up to 20 kg) or in any case 20 grams total.

DISCLOSURE OF EMBODIMENTS OF THE INVENTION

The invention provides a novel approach for determining and adjusting the schedule and dose of orally administered nitrogen scavenging drugs, including sodium phenylbutyrate and glyceryl tri-[4-phenylbutyrate] (HPN-100), based upon the urinary excretion of the drug metabolite phenylacetyl-glutamine (PAGN) and/or total urinary nitrogen. It is based in part on the discoveries that bioavailability of these drugs as conventionally assessed based on systemic blood levels of the drugs themselves or of the active species produced in vivo from these drugs does not accurately predict removal of waste nitrogen or reduction of plasma ammonia in healthy human volunteers, adults with liver disease, or patients with UCDs receiving ammonia scavenging drugs as defined below and that conversion of orally administered sodium phenylbutyrate (NaPBA, or sodium PBA) to PAGN to urinary PAGN is incomplete, typically about 60-75%. Prodrugs of phenylbutyrate (PBA, the active ingredient in BUPHENYL® (sodium phenylbutyrate), which is the sodium salt of PBA along with small amounts of inert ingredients), which is itself a prodrug of phenylacetic acid (PAA), are especially subject to the effects described herein.

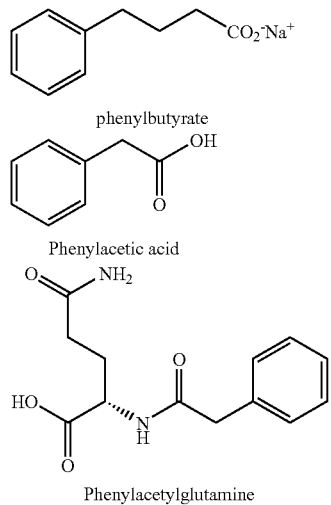

As used herein "ammonia scavenging drugs" is defined to include all orally administered drugs in the class which contain or are metabolized to phenylacetate. Thus, the term includes at least phenylbutyrate, BUPHENYL® (sodium phenylbutyrate), AMMONAPS®, butyroyloxymethyl-4-phenylbutyrate, glyceryl tri-[4-phenylbutyrate] (HPN-100), esters, ethers, and acceptable salts, acids and derivatives thereof. These drugs reduce high levels of endogenous ammonia by providing phenylacetic acid in vivo, which is metabolized efficiently to form phenylacetyl glutamine (PAGN). PAGN is efficiently excreted in urine, carrying away two equivalents of nitrogen per mole of PAA converted to PAGN. References herein to sodium phenylbutyrate are understood to include reference to the drug product BUPHE-NYL®, and BUPHENYL® was used for the Examples herein wherever test subjects were treated with sodium phenylbutyrate. Thus the sodium PBA dosages used in the Examples generally refer to a dosage of BUPHENYL®, and the amounts of sodium phenylbutyrate in those Examples should be interpreted accordingly. Note that the terms 'ammonia scavenger' and 'nitrogen scavenger' are used interchangeably in this invention, reflecting the fact that the drugs described herein lower blood ammonia through elimination of waste nitrogen in the form of PAGN.

In some embodiments, the invention uses prodrugs that can be converted into PAA within the body. Sodium phenylbutyrate (sodium PBA) is one such drug; it is converted by oxidative mechanisms into PAA in the body. HPN-100 is another such drug: it can be hydrolyzed to release PBA, which in turn can be oxidized to form PAA. Thus, HPN-100 is a prodrug of PBA, and also a prodrug of PAA. Clinical evidence demonstrates that HPN-100 is converted into PAA in the body as expected, and that PAA is then linked to a molecule of glutamine and converted into PAGN, which is eliminated in the urine as predicted. This process can be summarized as follows:

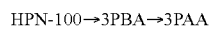

HPN-100→3PBA→3PAA

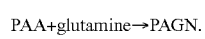

PAA+glutamine→PAGN.

PAGN is mainly excreted in the subject's urine, and removes two molecules of ammonia per molecule of excreted PAGN. Each HPN-100 molecule forms three PAA molecules, so each molecule of HPN-100 can promote excretion of six molecules of ammonia. The clinical results suggest that conversion of HPN-100 into PBA and PAA is efficient and fairly rapid, but surprisingly suggest that some conversion of HPN to PAGN may occur before the HPN-100 (or PBA, or PAA derived from PBA) enters systemic circulation. As a result, systemic levels of PAA or PBA are not reliably correlated with the efficacy of HPN-100 as an ammonia scavenger.

In some embodiments, the invention uses a prodrug of PBA, including HPN-100 and other esters of phenylbutyrate. The PBA prodrug is thus a prodrug of a prodrug, since PBA acts to scavenge ammonia after it is converted to PAA and is thus considered a prodrug of PAA. In some embodiments, the PBA prodrug is an ester of phenylbutyrate, such as those described below; a preferred PBA prodrug for use in the invention is HPN-100. These compounds can be made and used by methods disclosed in U.S. Pat. No. 5,968,979, which is incorporated herein by reference for its description of these compounds and methods for their administration.

Where an 'equal molar' or 'equimolar' amount of a second drug is to be used along with or instead of a certain amount of a first drug, the amount of each drug is calculated on a molar basis, and the equimolar amount of the second drug is the amount that produces an equal molar amount of active drug in vivo. Where one of the drugs is a prodrug, the amount of prodrug will typically refer to the molar amount of the active species formed from that prodrug. That active species is usually PAA for the prodrugs described herein, and the molar amount of a prodrug corresponds to the amount of PAA that would form in the body from that amount of the prodrug, assuming complete conversion into PAA occurs in vivo. Thus, for example, a molecule of HPN-100 can be metabolized by ester hydrolysis followed by oxidation to form three molecules of PAA, so a mole of HPN-100 would be considered equimolar to three moles of PAA. Similarly, since HPN-100 hydrolyzes to form three molecules of PBA (and one molecule of glycerin), an equimolar amount of HPN-100 would be one-third of the molar amount of PBA.

The following Table sets forth amounts of HPN-100 that correspond to equimolar amounts of certain relevant doses of BUPHENYL® (sodium phenylbutyrate). Note that the conversion of the dose of sodium PBA to the dose of HPN-100 involves correction for their different chemical forms [i.e. HPN-100 consists of glycerol in ester linkage with 3 molecules of PBA and contains no sodium; (sodium PBA [g]× 0.95=HPN-100 [g])] as well as correction for the specific gravity of HPN-100, which is 1.1 g/mL.

| BUPHENYL® (sodium PBA) | HPN-100 PBA Equivalent Dose (mg) | HPN-100 PBA Equivalent Dose (mL) |
|---|---|---|
| 450-600 mg/kg/day (patients ≤ 20 kg) | 428-570 mg/kg/day | 0.39-0.52 mL/kg/day |
| 9.9-13.0 g/m2/day (patients > 20 kg) | 9.4-12.4 g/m2/day | 8.6-11.2 mL/m2/day |
| Maximum Daily Dose: 20 g | Maximum Daily Dose: 19 g | 17.4 mL |

The present invention can use prodrugs of the formula (I):

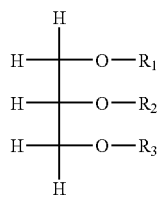
(I)

wherein $R_1$, $R_2$, and $R_3$ are independently, H,

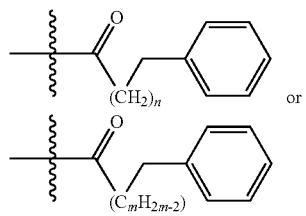

and n is zero or an even number, m is an even number and at least one of $R_1$, $R_2$, and $R_3$ is not H. For each $R_1$, $R_2$, or $R_3$, n or m is independently selected, so the $R_1$, $R_2$, and $R_3$ groups in a compound of formula I do not have to be identical. The preferred compounds are those wherein none of $R_1$, $R_2$, and $R_3$ is H, and frequently each n or m for a particular embodiment is the same, i.e., $R_1$, $R_2$, and $R_3$ are all the same. The advantage over the prior art of decreased dosage is greater with such triesters, and having all three acyl groups the same reduces issues related to mixtures of isomers. Moreover, the triol backbone liberated by hydrolysis of the esters is glycerol, a normal constituent of dietary triglyceride which is non-toxic.

The present invention also utilizes phenylbutyrate and phenylacetate prodrugs of the formula II:

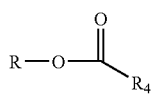
(II)

wherein R is a $C_1$-$C_{10}$ alkyl group,
$R_4$ is

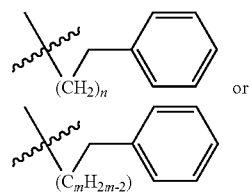

and n is zero or an even number, and m is an even number.
In Formula II, R can be, for example, ethyl, propyl, isopropyl, n-butyl, and the like.

The compounds of the invention are esters of the congeners of phenylalkanoic and phenylalkenoic acids having an even number of carbon atoms in the alkanoic acid portion, which include phenylacetic acid esters and those of phenylbutyric acid, etc., which can be converted by efficient beta-oxidation processes to phenylacetic acid in the body. They are thus prodrugs for phenylacetic acid. Where n is 2 or 4, the esters are also prodrugs for phenylbutyric acid. Preferably the alkylene or alkenylene carboxylate group contains 24 or fewer carbon atoms, so n or m is less than 24. In some embodiments, n and m are 0, 2, 4 or 6, and in some preferred embodiments n or m is 2.

Certain preferred embodiments of the invention use HPN-100 (Formula III):

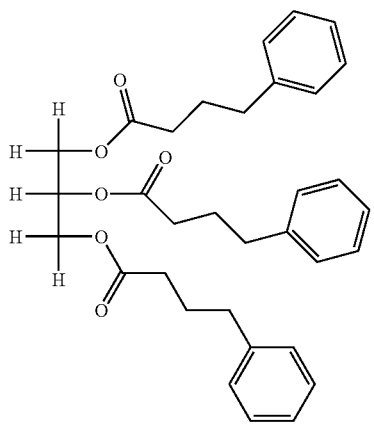
(III)

Total daily dosage of prodrugs like sodium PBA can often be selected according to the amount needed to provide an appropriate amount of the active species, if that amount is known or can be determined. PBA is a prodrug for PAA; therefore, an initial dose of PBA could be selected if an effective dosage of PAA were known, taking into account the fraction of PBA that is converted into PAA and ultimately into PAGN. If a subject has been treated with PAA or a prodrug that forms PAA in the body, the amount of the previously used drug that was effective provides a possible starting point for selecting a dosage of a new prodrug of PAA. In this same patient, after the new prodrug is administered at the expected PAA dose equivalence, the PAA levels in the subject could be monitored and the dose of the prodrug adjusted until the same plasma level of PAA that was effective with the previous treatment is achieved. However, the current invention is based in part on finding that plasma PAA and PBA levels are not well correlated with the dose of a PBA prodrug administered or with ammonia elimination; for monitoring a dosing level of a PBA prodrug, one should not rely upon these parameters to assess the effectiveness of the prodrug. While not bound by the underlying theory, explanations for this effect (i.e. the inconsistent relationship between ammonia scavenging and PBA and/or PAA blood levels) are provided herein.

The following Table provides data from three clinical test groups showing the inconsistent relationship between plasma PAA and PBA levels among healthy volunteers, patients with cirrhosis and UCD patients, despite that fact that, as described in detail below, all groups exhibited similar ammonia scavenging activity based on urinary excretion of PAGN. Overall, this shows that urinary PAGN provides a convenient method for monitoring ammonia elimination induced by the administered drug, which does not require drawing blood and directly relates to the actual nitrogen elimination provided by the administered nitrogen scavenging drug without being influenced by the many other factors that can affect plasma ammonia levels.

Plasma Pharmacokinetics of PBA, PAA, and PAGN Comparison across Studies

| Analyte | Treatment | $C_{max}$ (µg/mL) | $T_{max}$ (h) | $T^{1/2}$ (h) | $AUC_{24}$ (µg · h/mL) |
|---|---|---|---|---|---|
| Healthy Volunteers (Single Dose - 3 g/m²/day PBA Mole Equivalent) | | | | | |
| PBA | Sodium PBA | 221.0 | 0.9 | 0.7 | 542.6 |
| | HPN-100 | 37.0 | 2.4 | 1.9 | 137.2 |
| PAA | Sodium PBA | 58.8 | 3.9 | 1.2 | 279.8 |
| | HPN-100 | 14.9 | 4.0 | NC | 70.9 |
| PAGN | Sodium PBA | 63.1 | 3.2 | 1.7 | 395.1 |
| | HPN-100 | 30.2 | 4.0 | NC | 262.1 |
| Healthy Volunteers and Cirrhotic Patients (100 mg/kg BID)[1] | | | | | |
| PBA | Child-Pugh A | 42.8 | 2.3 | 1.2 | 131.7 |
| | Child-Pugh B | 41.8 | 2.9 | 3.4 | 189.5 |
| | Child-Pugh C | 44.3 | 3.1 | 1.9 | 192.1 |
| | Volunteers | 29.8 | 3.0 | 2.1 | 132.7 |
| PAA | Child-Pugh A | 33.2 | 3.8 | 1.8 | 168.8 |
| | Child-Pugh B | 30.8 | 4.5 | 2.8 | 252.4 |
| | Child-Pugh C | 53.1 | 4.8 | 7.7 | 579.9 |
| | Volunteers | 25.5 | 3.6 | 1.9 | 130.5 |
| PAGN | Child-Pugh A | 37.7 | 3.9 | 5.0 | 335.1 |
| | Child-Pugh B | 38.1 | 4.0 | 7.5 | 466.99 |
| | Child-Pugh C | 43.1 | 5.3 | 4.0 | 578.4 |
| | Volunteers | 46.3 | 4.3 | 7.2 | 550.9 |
| UCD Subjects (Multiple Dose - PBA Mole Equivalent) | | | | | |
| PBA | Sodium PBA | 141.0 | 2.1 | NC | 739.0 |
| | HPN-100 | 70.1 | 6.1 | NC | 540.0 |
| PAA | Sodium PBA | 53.0 | 8.1 | NC | 595.6 |
| | HPN-100 | 40.5 | 8.0 | NC | 574.6 |
| PAGN | Sodium PBA | 83.3 | 7.2 | 3.9 | 1133.0 |
| | HPN-100 | 71.9 | 8.0 | 4.8 | 1098.0 |

$C_{max}$ = maximum plasma concentration;
$T_{max}$ = time of maximum plasma concentration;
$AUC_{24}$ = AUC from time 0 to 24 hours;
NC = not calculated
[1]Study did not include a sodium phenylbutyrate comparator arm, values represent HPN-100 dosing only. AUC values represent the AUC from time 0 to the last measurable plasma concentration.

One embodiment of the invention is a method for determining and/or adjusting the dose of ammonia scavenging drugs in patients with UCDs, whereby dose would be based on the amount of dietary protein the patient is consuming, the anticipated percentage conversion of the drug to PAGN, and the patient's residual urea synthetic capacity, if any. Dose adjustments, if necessary, would be based on the observed urinary excretion of PAGN and/or total urinary nitrogen (TUN), the difference between the two reflecting the patient's endogenous capacity for waste nitrogen excretion. This endogenous capacity may be absent in certain patients having innate urea cycle disorders due to inborn metabolic deficiencies, but patients with later-onset nitrogen accumulation disorders generally have some endogenous capacity, referred to sometimes as their residual urea synthesis capacity. See Brusilow, PROGRESS IN LIVER DISEASES, Ch. 12, pp. 293-309 (1995). The subject's plasma ammonia level may also be determined; this is a critical parameter for tracking effectiveness of an overall treatment program, but reflects a variety of factors such as dietary protein and physiological stress, as well as the effect of a drug used to promote nitrogen excretion.

Once the patient's residual endogenous capacity for waste nitrogen excretion has been determined, either as the difference between PAGN output and total nitrogen output or as total urinary nitrogen output in the absence of an ammonia scavenging drug, the tolerable amount of dietary protein can be calculated for that patient according to the dosage of the ammonia scavenging drug being administered, or the dosage of the ammonia scavenging drug can be adjusted or calculated to compensate for an estimated protein intake.

Another embodiment is a method for determining and adjusting the dose of an ammonia scavenging drug to be administered to a patient with liver disease, including hepatic encephalopathy, whereby the starting dose would be based on the amount of dietary protein the patient is consuming, the anticipated conversion of the drug to PAGN, and the patient's residual urea synthetic capacity, if any. While the urea synthetic capacity in patients with liver disease would generally be greater than for patients with UCDs, considerable patient to patient variability would be expected among both groups depending, respectively, on the severity of their liver disease and the severity of their inherited enzymatic defect. Dose adjustments based on the observed urinary excretion of PAGN and total waste nitrogen would adjust for these individual patient characteristics.

Another embodiment is a method for determining or adjusting allowable dietary protein in the diet of a patient with UCD or with hepatic encephalopathy, who is being treated with an oral PAA-forming ammonia scavenging drug, whereby the amount of allowable protein would be determined by the amount of PAGN and total nitrogen in the urine.

The difference between total waste nitrogen in the urine and the amount of PAGN excreted is indicative of the patient's endogenous waste nitrogen processing capacity. Once the patient's endogenous nitrogen processing capacity is known, the patient's endogenous nitrogen processing capacity can be used to adjust dietary protein intake while administering a fixed dosage of an ammonia scavenging drug, or the dosage of the ammonia scavenging drug can be determined according to the amount needed to facilitate elimination of the waste nitrogen from the patient's dietary protein. Dietary protein intake should be determined or adjusted according to how much nitrogen the subject can eliminate above the amount that is eliminated as PAGN, which results from the PAA-forming ammonia scavenging drug being administered. When making these calculations or adjustments, it is suitable to assume that about 47% of nitrogen in protein will become waste nitrogen that needs to be excreted in the urine (the amount may be less for growing patients, who retain a greater fraction of ingested nitrogen to support body growth), and that about 16% of protein, on average, is nitrogen (see Brusilow 1991).

It has generally been assumed for such determinations that a prodrug would be converted with 100% efficiency into PAGN for elimination [see, e.g., Berry et al., *J. Pediatrics* 138(1), S56-S61 (2001) where FIG. 1 assumes 100% conversion]; and one report found that about 80-90% of PAA or PBA was excreted from a specific individual as PAGN. Brusilow, *Pediatric Research* 29(2), 147-150 (1991). It has now been found that HPN-100 and phenylbutyrate are both converted into urinary PAGN at an overall efficiency of about 60% to about 75% on average (about 60% conversion efficiency was seen in UCD patients and about 75% conversion was seen in cirrhotic patients, for example); consequently, this efficiency factor can be used to more accurately calculate or determine initial dosing levels for these drugs, or dietary protein levels acceptable for patients who use these drugs. Given this conversion rate, each gram of HPN-100 can facilitate elimination of waste nitrogen from about a gram (~1.3 grams) of dietary protein per day. Note that PAGN carries away two molecules of ammonia per molecule of PAGN. Examples of calculations based on these parameters are provided in Examples 9 and 10 herein.

In one aspect, the invention provides a method for transitioning a patient from phenylacetate or phenylbutyrate to HPN-100 or other esters or prodrugs of phenylbutyrate. The method involves administering an initial dosage of the prodrug that is selected based on the patient's current dosage of phenylacetate or phenylbutyrate, and is adjusted according to the levels of excreted PAGN that result when the prodrug is administered.

In some embodiments, the transition from phenylbutyrate might be undertaken in more than a single step and urinary excretion of PAGN and total nitrogen would allow monitoring of ammonia scavenging during the transition (e.g. for clinically 'fragile' patients with a propensity for frequent hyperammonemia). The methods can use two, three, four, five, or more than five steps as judged clinically prudent. At each step, a fraction of the initial dosage of phenylbutyrate corresponding to the number of steps used for the transition is replaced by an appropriate, amount (i.e. the amount necessary to deliver an equimolar amount of PBA) of HPN-100 or other prodrug of phenylbutyrate, e.g., if the transition is to be done in three steps, about one-third of the phenylbutyrate would be replaced with a prodrug at each step.

Another embodiment of the invention is based on observations that delivery of PBA in the form of a glyceryl tri-ester or other prodrug imparts slow release characteristics that allow greater flexibility in dosing schedule. Sodium phenylbutyrate (sodium PBA), for example, is typically dosed every 4 to 8 hours, or even more frequently, in order to maintain a suitable plasma level of PAA. This regimen reflects the rapid absorption of phenylbutyrate from the gastrointestinal tract and quick metabolic conversion to PAA. HPN-100, by contrast, which is a glyceryl tri-ester of phenylbutyrate, has been found to be absorbed only 40% as rapidly as sodium PBA, enabling dosing three times daily, such as with meals, or even twice daily, such as morning and evening. This dosing flexibility is further enhanced by the fact that the pharmacokinetic (PK) and pharmacodynamic (PD) properties of HPN-100 are indistinguishable in the fed or fasted states. It is thus not critical for the frequency of administration to be rigidly maintained with the PBA prodrugs in the form of an ester; the number of doses per day can be reduced for greater convenience, and the dosages do not have to be linked to meal schedules as is recommended in the label for sodium PBA. Indeed, pharmacokinetics for utilization of HPN-100 were very similar when HPN-100 was taken with food or without food, after a day of fasting, so HPN-100 can be taken with food or without food. This translates into a more convenient treatment protocol and potentially higher patient compliance upon substituting HPN-100 for phenylbutyrate or phenylacetate. Surprisingly, even though HPN-100 and sodium PBA are both prodrugs of PAA, HPN-100 is effective when administered less frequently than sodium PBA. While it is typically necessary to administer smaller doses of sodium PBA 3-6 times per day to maintain a stable level of plasma ammonia, similar results can be achieved with only 2-3 doses of HPN-100 per day. In some embodiments discussed in greater detail below, HPN-100 is administered in two doses per day (BID), and in some embodiments it is administered in three doses per day (TID).

It has also been found that because of the slow-release characteristics of HPN-100, a patient taking HPN-100 has more sustained and often lower plasma levels of PBA and PAA than a patient taking sodium PBA itself. This is believed to be consistent with the greater flexibility in dosing that is discussed in more detail elsewhere in this application (plasma levels of PBA rise and fall more quickly after administration of sodium PBA than after administration of HPN-100).

Other aspects of this invention relate to the observation that there is apparently no saturation in the ability of the body to convert sodium PBA or HPN-100 to urinary PAGN over a several-fold dose range up to and including, the maximum doses of sodium PBA recommended to date. This should enable a patient to take a higher dose of HPN-100 than an equimolar amount compared to the patient's dosage of PBA. It suggests a patient can receive a higher dosage of HPN-100 than those dosages of sodium PBA that have been recommended to date, which is especially useful for patients whose ammonia levels were not adequately controlled by the highest labeled dosages of sodium PBA. Such patients can receive doses of HPN-100 that are higher than previously recommended sodium PBA dosages.

Other aspects of the invention will be apparent from the following detailed description and the examples provided herein.

For convenience, the amounts of PAA (phenylacetic acid), PBA (phenyl butyric acid), or HPN-100 to be administered to a subject as discussed herein refer to a total daily dosage. Because these compounds are used in relatively large daily amounts, the total daily dosage may be taken in two, three, four, five, or six, or more than six daily doses, and different drugs may be administered on different schedules. Thus the total daily dosage better describes a treatment regimen with one drug for comparison to treatments with related drugs.

BRIEF DESCRIPTION OF THE DRAWINGS

FIG. 3 depicts an adapted model to describe PK behavior of sodium PBA or other drugs such as HPN-100 that can be converted to PBA and PAA, informed by the observations described herein showing that metabolism of HPN-100 results in lower plasma levels of PAA and PBA while providing equivalent pharmacological effect. Unlike the conventional model, this model allows for 'pre-systemic' conversion of PBA/PAA to PAGN and explains inconsistent relationship between blood levels of these metabolites and PAGN-mediated excretion of waste nitrogen FIG. 4 shows how plasma levels of PAA, PBA, and PAGN change over time following administration of a single dose of either PBA or HPN-100. It shows that the peak level of PAA is lower when the PBA prodrug, HPN-100, is used, and the PAA level at 24 hours post-administration is higher with the prodrug. Thus the prodrug provides a more sustained level of plasma PAA.

FIGS. 9a, 9b, and 9c show that in subjects treated with HPN-100, there is little or no correlation between the dose of HPN-100 and plasma levels of either PBA or PAA in the subject. However, it also shows that urinary excretion of PAGN correlates well with dosage of HPN-100.

MODES OF CARRYING OUT THE INVENTION

Figure 1:
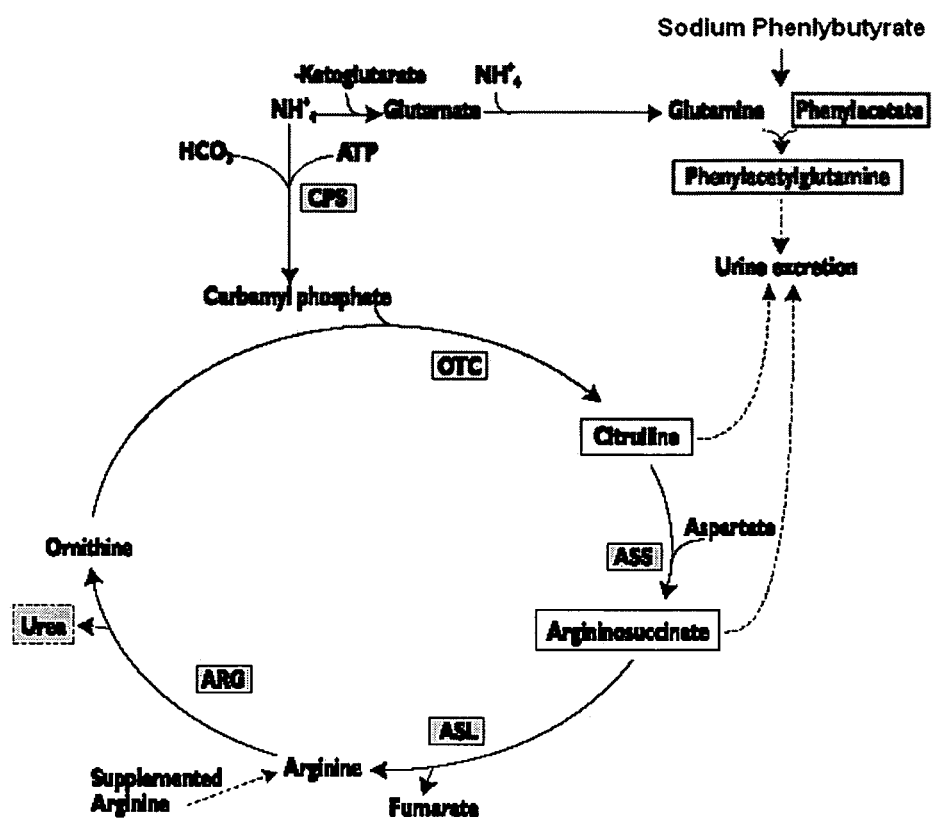
FIG. 1 shows waste nitrogen disposal via the urea cycle and by the auxiliary pathway involving PAGN.

In one aspect, the invention is reduced to practice in determining the dose, dosing schedule and dose adjustments necessary for treatment of nitrogen retention states including urea cycle disorders and liver disease complicated by hepatic encephalopathy. The starting dose and schedule would be based upon the theoretical considerations including the estimated percentage conversion of the drug to PAGN, the waste nitrogen resulting from the patient's dietary protein and the percentage of drug converted to and excreted as PAGN. Following initiation of treatment, further dose adjustments would then be made if necessary, upon the actual measurement of urinary PAGN output, or a well-correlated parameter like total urinary ammonia or the ratio of PAGN to creatinine.

In another aspect, the invention provides a method to transition a patient from phenylbutyrate or phenylacetate to a prodrug of phenylbutyrate (which is a prodrug of PAA), such as HPN-100, or other ester or prodrugs such as compounds of Formula I and II as shown herein. For a number of reasons, HPN-100 is considered a more desirable drug than sodium PBA for many patients who have high ammonia levels and require treatment with an ammonia scavenging drug. In particular, it avoids the unpleasant taste associated with sodium PBA, and it reduces potentially harmful sodium intake, since phenylbutyrate is administered as a sodium salt. A large majority of patients (nine out of ten UCD patients who participated in the clinical study described in example 3) preferred HPN-100 over sodium PBA in clinical testing. Thus many patients who have been treated with phenylbutyrate as an ammonia scavenging drug may want to transition from it to HPN-100.

It would seem logical for a physician to transition a patient from phenylbutyrate to a prodrug of phenylbutyrate by calculating the amount of the prodrug that would produce an amount of PBA that corresponds to the dosage of phenylbutyrate previously administered to the patient. This would be expected to produce about the same blood plasma level of the active ingredient, PBA. Efficacy of the new treatment with the prodrug could then be assessed by monitoring levels of phenylbutyrate in the blood, to establish the same levels achieved when PBA was administered. As discussed below, however, that approach is not appropriate because, surprisingly, plasma levels of PBA do not correlate well with administered dosages of HPN-100 or with the effectiveness of a dose of HPN-100 or sodium PBA. (Note that sodium PBA is the acid form of phenylbutyrate, which is the common name for the drug BUPHENYL®, and is typically administered as BUPHENYL®, which is a sodium salt of PBA. References to treatment with PBA herein encompass administration of the phenylbutyrate neutral compound or a salt of phenylbutyrate. Typically, and in all of the working examples herein, PBA is administered as BUPHENYL®.)

Alternatively, since PBA is a prodrug for PAA, the dosage of a phenylbutyrate prodrug could be calculated according to the theoretically formed amount of PAA, which should be the same amount as what would be calculated from the PBA dosage, since one molecule of PBA is expected to produce one molecule of PAA. The molecular weight of sodium PBA, the registered drug form of PBA (the sodium salt of PBA), is 186; the molecular weight of HPN-100 is 530, and of course HPN-100 provides three equivalents of PBA per molecule, so only one-third as many moles of HPN-100 would be needed to replace a molar quantity of either PBA or PAA. Thus each gram of sodium PBA could be replaced by 0.95 grams of HPN-100; and since HPN-100 is a liquid having a density of 1.1 g/mL, each gram of sodium PBA would be replaced by 0.87 mL of HPN-100, assuming HPN-100 is used as an undiluted liquid. This can be used to select a starting dosage of HPN-100 for patients being transitioned from sodium PBA to HPN-100. Alternatively, a starting dose of HPN-100 in a patient not already taking BUPHENYL® (sodium phenylbutyrate) would need to take into account the surprising observation described in more detail below (see examples 2 and 3) that conversion of the PBA, when administered as HPN-100, into urinary PAGN is incomplete and averages about 60-75%.

Alternatively, the physician could measure plasma levels of either PBA or PAA in a subject receiving an effective amount of PBA, and determine a dosage of a PBA prodrug by administering enough of the prodrug to produce the same plasma levels of PBA or PAA. The physician could then monitor the amount of either PBA or PAA in the blood to ensure that the appropriate amount of active drug was being produced in the body. It might be expected that a prodrug of phenylbutyrate would provide a slightly lower blood plasma concentration of PAA or PBA than phenylbutyrate, and thus a lower nitrogen-scavenging effect, since conversion of the prodrug to the active drug might be less than 100% efficient. Thus monitoring PAA or PBA plasma levels and increasing the prodrug dosage to bring levels up to those obtained by administering phenylbutyrate might be expected to produce the same physiological effect as the phenylbutyrate dosage. However, it was found that it is not necessary for the plasma level of PAA or PBA observed upon administration of a prodrug of phenylbutyrate to match that produced by an effective amount of phenylbutyrate, in order to achieve the same ammonia-scavenging effect. Rather, efficacy of the prodrug HPN-100 correlates with urinary PAGN levels, not with plasma levels of PAA or PBA.

Figure 2:
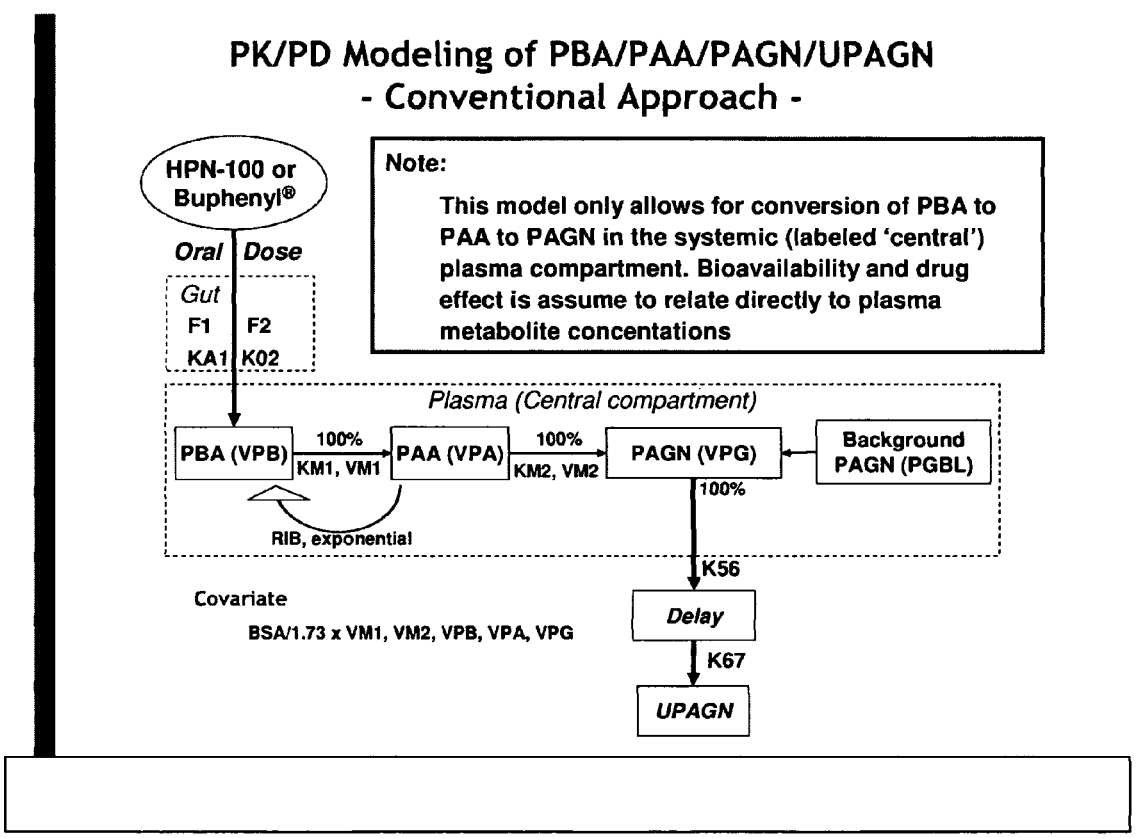
FIG. 2 depicts a conventional model to describe pharmacokinetic (PK) behavior of a prodrug, which, in the case of phenylbutyrate, assumes that PBA and PAA must reach the systemic circulation in order to be active; i.e., in order to be converted to PAGN and effect ammonia scavenging.

Models have been developed to describe how ammonia-scavenging drugs or prodrugs are expected to behave in vivo. One model, shown in FIG. 2, reflects conventional approaches to assessing drug effectiveness as applied to HPN-100 based on blood levels of PAA or PBA. Clinical testing has shown that HPN-100 does not produce the plasma levels of PAA and PBA that might be expected from this model, though, even though it is at least as effective on an equimolar basis as PBA for controlling blood ammonia levels, and for eliminating ammonia as PAGN via the urine. Thus the conventional model fails to account for some important metabolic differences between PBA and HPN-100. It was hypothesized that, as compared with sodium PBA, a greater percentage of PBA derived from HPN-100 is converted into PAGN for elimination (or PAA or PBA derived from it) before entering the systemic circulation (the "central compartment" in FIG. 2). Recognition of this important and unexpected difference underlies certain aspects of the present invention.

A refined working model based upon the observations described herein and as outlined in this disclosure is depicted in FIG. 3. It supports the conclusion that PBA derived from HPN-100 as well as from sodium PBA can be converted into PAGN without entering into systemic circulation; presumably, HPN-100 or its initial metabolic products (e.g., a compound of formula I wherein one or two of $R_1$-$R_3$ represent phenylbutyryl groups, and the remaining one or two of $R_1$-$R_3$ represent H—the expected products of partial hydrolysis of HPN-100) may reach the liver and be converted into PAGN there, prior to reaching the systemic circulation. Moreover, the fractional conversion of PBA derived from HPN-100 is greater than for PBA absorbed when PBA is administered as the salt, an observation which explains the lower blood levels of PBA following administration of HPN-100 as compared with sodium PBA despite equivalent or potentially superior ammonia scavenging activity. This observation led to the recognition that plasma levels of PAA or PBA are not reliable indicators of the effectiveness of a PBA prodrug like HPN-100, and should not be relied upon to set or adjust dosages of such PBA prodrug compounds. Data presented herein, e.g. as summarized in FIG. 9, demonstrate this effect. Alternative methods for monitoring a subject treated with HPN-100 are needed, and are provided herein.

Figure 6:
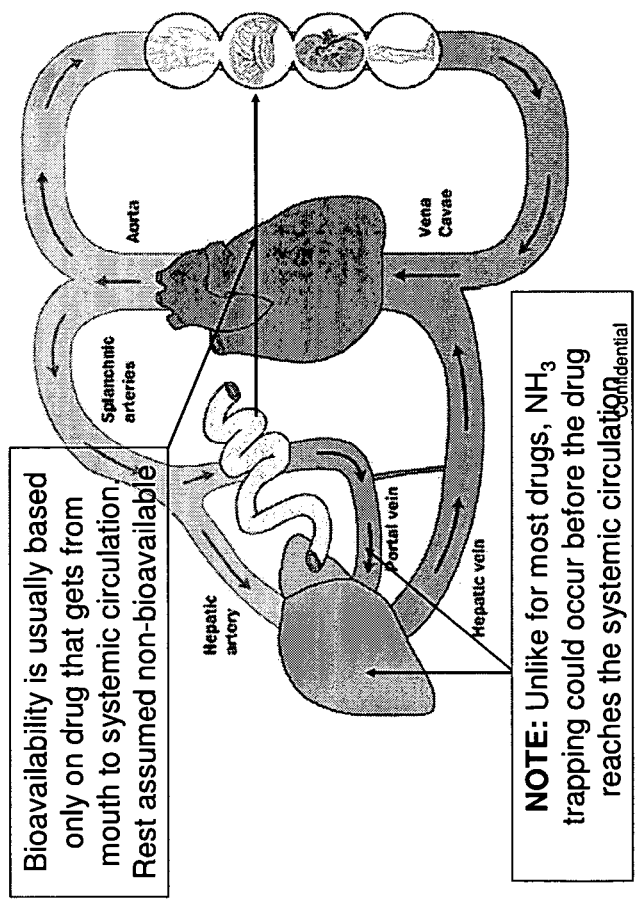
FIG. 6 presents an anatomic explanation for the observations that the prodrug (PBA) can be converted to PAGN prior to reaching the systemic circulation (corresponds to the model depicted in FIG. 3).
Figure 7:
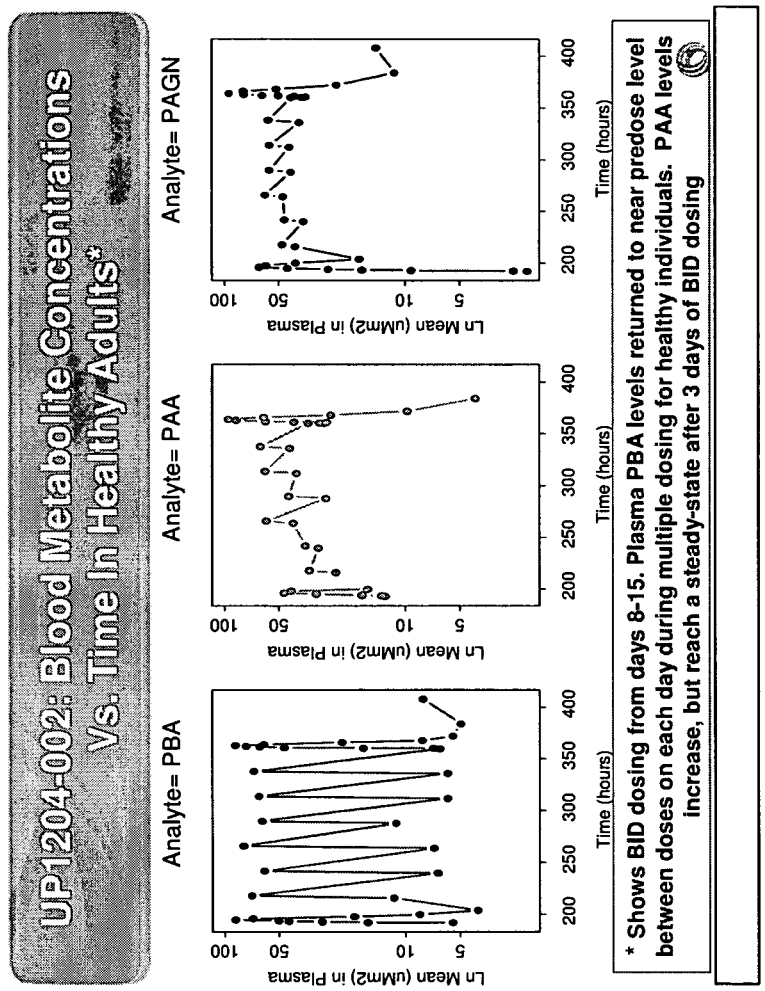
FIG. 7 shows that PBA levels fluctuate relatively rapidly after dosing in healthy adults, while PAA and PAGN levels reach a fairly stable state after a few days of treatment with sodium phenylbutyrate.
Figure 8:
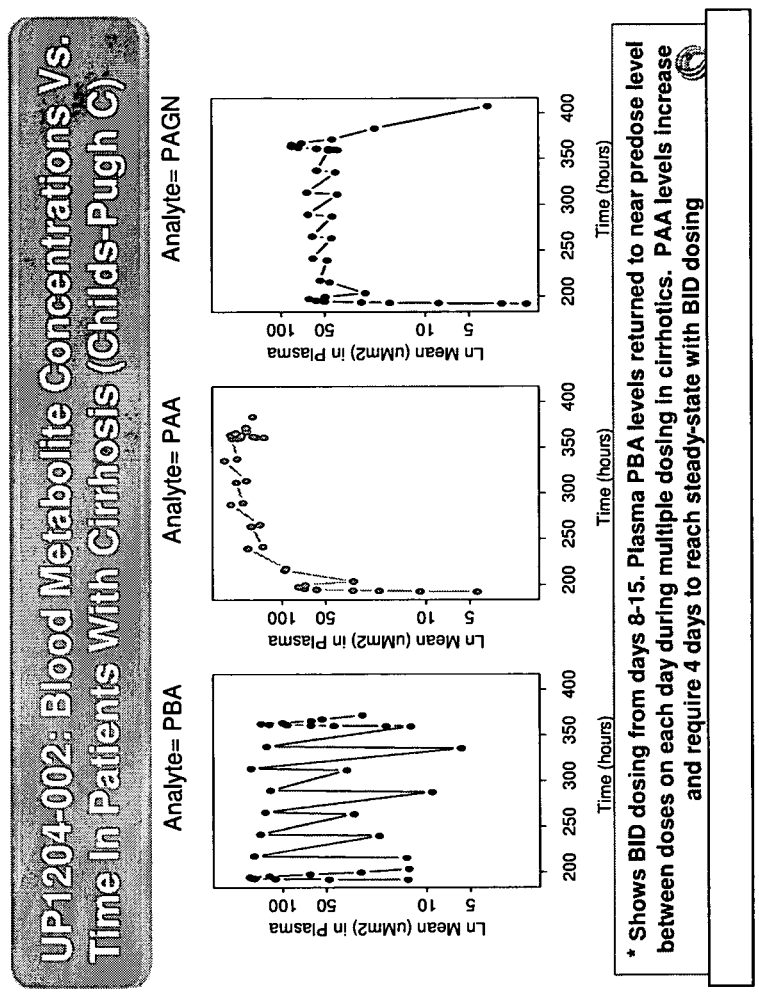
FIG. 8 shows that PBA, PAA and PAGN levels reach steady states at different times in healthy adults and that PAA takes longer to reach a steady state level in cirrhotics

In addition, PK/PD modeling, as reflected by considerations and depicted in FIGS. 3 and 6, demonstrate that HPN-100 is absorbed only about 40% as rapidly as PBA when dosed orally. As a result, HPN-100 provides a slow-release delivery effect, even though it appears to metabolize to PBA rapidly once absorbed. This provides greatly flexibility in dosing and explains why HPN-100 can be dosed, e.g., three times per day or even twice per day to provide similarly stable ammonia levels that require four or more doses of PBA to achieve.

In view of these observations of unexpected pharmacokinetic behavior, plasma PAA and PBA levels should not be used to evaluate or monitor treatment of a subject with HPN-100 or sodium PBA. Alternative methods are needed, and are provided herein, for monitoring a subject treated with HPN-100. For one, it has been found that between 50 and 85% of HPN-100 is converted into urinary PAGN, typically about 60% to about 75%. This conversion efficiency for HPN-100 and sodium PBA in UCD patients is surprising in light of previous references that have generally assumed the conversion efficiency of sodium PBA to be about 100%. Urinary PAGN has been shown to be inversely correlated with levels of waste nitrogen, e.g. ammonia, in the blood, thus efficacy of HPN-100 can be evaluated by measuring urinary PAGN. It has also been found that HPN-100 has little to no effect on creatinine levels. Moreover, because creatinine levels in healthy adults and patients with nitrogen retention states are typically rather stable, either measuring PAGN output in urine over time, or measuring the ratio of the concentrations of PAGN to creatinine, which can be conveniently done in spot testing, provides a way to monitor HPN-100's effectiveness. In one aspect, the invention thus provides a method to assess the effectiveness of a treatment with HPN-100, comprising determining the ratio of PAGN to creatinine in a 'spot urine' test. Clinical studies show that urinary excretion of PAGN, and the ratio of PAGN to creatinine in urine, correlate well with blood ammonia levels: an increase of PAGN or of the PAGN/creatinine ratio correlates with decreasing plasma ammonia levels. Accordingly, in one method, HPN-100 treated patients are monitored by measuring urinary PAGN output, or by measuring the ratio of PAGN to creatinine in spot urine testing. This method can be used to monitor treatment of a treatment-naïve patient, or of a patient being transitioned from PBA to HPN-100, or a patient being treated with HPN-100. Increasing levels of urinary PAGN output, or an increase in the ratio of PAGN to creatinine in spot testing provides a way to determine whether a dosing regimen that utilizes HPN-100 or another PBA prodrug is promoting elimination of excess ammonia, and to compare two treatment methods to determine which is more effective for the particular subject.

While plasma ammonia levels are often used to assess disease control in UCD patients, it is often inconvenient to rely upon plasma ammonia levels for optimizing the dosing of HPN-100 outside of a clinical setting. Moreover, plasma ammonia levels are affected by many factors and might be elevated regardless of how well a drug treatment works; it reflects dietary and other factors as well as the adequacy of a drug dosage being used. Plasma ammonia varies a good deal even when relatively well-controlled, based on meal timing, drug timing, and various other factors. Thus to meaningfully reflect drug effect, the plasma ammonia levels need to be monitored over time by repeated blood samplings, which is not practical for routine monitoring of some patients and which does not provide direct information about whether an ammonia scavenging drug is working. Measurements of urinary PAGN, on the other hand, can be done more conveniently as a routine monitoring method because they do not require medical assistance to collect the samples for testing. Moreover, urinary PAGN specifically measures the waste nitrogen clearance provided by the scavenging agent, while many other factors affecting ammonia levels may cause ammonia control to be misleading with regard to the actual effect of the nitrogen scavenging drug. Thus, even though in theory a number of different parameters could be measured to assess effectiveness of a dosage of HPN-100, only measurements based on urinary PAGN are both convenient and reliable as a direct measurement of the nitrogen scavenging drug's effect.

Thus in one embodiment, the invention provides a method to monitor the effectiveness of treatment of a UCD patient with HPN-100, where monitoring consists essentially of monitoring the patient's urinary PAGN excretion, and optionally checking plasma ammonia levels. Urinary PAGN levels comparable to those achieved with a previous PBA dosing regimen would be considered evidence that the HPN-100 treatment was equally effective as the PBA treatment it replaced. Alternatively, a plasma ammonia level of less than about 40 μmol/L, or of not greater than 35 μmol/L would indicate the treatment was effective. In some embodiments, rather than using urinary PAGN output measured over time, one can use the ratio of PAGN to creatinine in the urine, in a spot test.

In another aspect, the invention provides a utilization efficiency factor for HPN-100 or for sodium PBA of about 60% to about 75%, which can be used to more accurately determine an initial starting dose of either drug and/or correlate dietary protein intake with projected urinary PAGN.

In one aspect, the invention provides a method for transitioning a patient from phenylbutyrate to HPN-100 or other esters or prodrugs of phenylbutyrate. The method involves administering an initial dosage of the prodrug that is selected based on the patient's current dosage of phenylbutyrate. For example, the amount of HPN-100 needed to provide an equal molar amount of PBA would be calculated (an equimolar amount), and this equimolar amount would be administered to the patient. Urinary excretion of PAGN or plasma ammonia levels would be monitored, and the dosage of HPN would be increased or decreased as needed to establish a level of PAGN excretion that is about the same as that provided by a previously used effective amount of phenylbutyrate or another nitrogen scavenging drug. Typically, a subject being transitioned from PAA or another PAA prodrug onto HPN-100 using this method would be tested for urinary PAGN output prior to the transition and afterwards, and the dosage of HPN-100 would be adjusted as needed to match the urinary PAGN output from this patient when treated with the previous PAA drug or prodrug, assuming the previous PAA prodrug treatment was considered effective. This provides a safer and more effective transition to the new prodrug than methods that rely upon using an equimolar amount without monitoring the in vivo effects of that amount of the new drug. It also avoids the risk of inaccurate dosing and potential overtreatment that could result if one monitored PAA or PBA and tried to adjust the prodrug (i.e. HPN-100) dosage to match the PAA or PBA level to the corresponding level provided by administering sodium phenylbutyrate itself.

In some embodiments, the transition from phenylbutyrate might be undertaken in more than a single step and urinary excretion of PAGN and total nitrogen would allow monitoring of ammonia scavenging during the transition. In some embodiments, a patient taking an initial dosage of phenylbutyrate is transitioned from phenylbutyrate to a prodrug of phenylbutyrate in steps. The methods can use two, three, four, five, or more than five steps. At each step, a fraction of the initial dosage of phenylbutyrate corresponding to the number of steps used for the transition is replaced by an appropriate amount of HPN-100 or other prodrug of phenylbutyrate. The appropriate amount for each step can be approximately an amount sufficient to provide an equal molar amount of PBA if it is assumed that the prodrug is quantitatively converted into PBA. Note, too, that BUPHENYL® (sodium phenylbutyrate) contains about 6% inactive ingredients, so it is appropriate to base calculations upon the PBA content of the drug rather than on the weight of the formulated drug. The patient is then monitored to determine how much ammonia scavenging effect has been provided. The amount of HPN-100 (or prodrug) can then be adjusted to produce about the same amount of ammonia excretion in the form of excreted PAGN that was achieved by the initial dosage of phenylbutyrate, if the patient was well controlled.

A physician who is switching a patient from PBA to HPN-100 or another ester of phenylbutyrate should be aware that an effective amount of HPN-100 does not necessarily produce a PAA or PBA level that is as high as those seen when sodium phenylbutyrate is administered. It is reported that PAA exhibits some toxicity at high plasma concentrations. Thibault, et al., *Cancer Research*, 54(7):1690-94 (1994) and *Cancer*, 75(12):2932-38 (1005). Given this, and given the unique properties of HPN-100 described above, it is particularly important that a physician not use plasma levels of PAA or PBA to measure the efficacy of HPN-100. If one administers HPN-100 in amounts sufficient to match the plasma PBA or PAA levels provided by administering phenylbutyrate, for example, the dose of HPN-100 may be unnecessarily high.

The treatment-naïve patient is one not presently receiving an ammonia-scavenging drug treatment to manage nitrogen levels. While there are recommended dosage levels for the nitrogen scavenging drugs in many cases, the right dosage for a naïve patient may be lower than those ranges, for example, and, less commonly, it may be above an equimolar amount when compared to the dosages recommended for sodium PBA. The initial dosage of PAA or a PAA prodrug can be calculated by methods known in the art once a patient's dietary intake of protein is known, and assuming the patient has a relatively normal liver function. Saul W Brusilow, "Phenylacetylglutamine may replace urea as a vehicle for waste nitrogen excretion," *Pediatric Research* 29:147-150, (1991). Methods are also know for measuring the total amount of nitrogen excreted in the urine; in the case of a subject taking a drug that acts by providing PAA, the total waste nitrogen will include PAGN excreted.

It is estimated that about 47% of nitrogen in proteins consumed will be converted into waste nitrogen, and that about 16% of protein on average is nitrogen. Using these figures, and assuming HPN-100 is efficiently converted to PAGN, a daily dosage of about 19 g of HPN-100 would provide a vehicle to excrete the waste nitrogen from about 43 g of dietary protein; each gram of HPN-100 would thus be able to carry away waste nitrogen from about 2 g of dietary protein. In addition, if it is estimated that HPN-100 utilization efficiency is between about 50% and 85% in various individual patients (as disclosed herein, it has been found that about 60-75% of HPN-100 is converted into urinary PAGN on average), which is consistent with clinical observations to date, and these factors can be used to further refine the relationship between dietary protein intake and HPN-100 dosing levels for a given subject. With this refinement, each gram of HPN-100 would assist with removal of waste nitrogen for about 1 gram (~1.3 grams) of dietary protein. This factor can be used to calculate a suitable dosage of HPN-100 if dietary protein intake is known or controlled, and it can be used to calculate a tolerable dietary protein intake for subject receiving HPN-100.

This method can also be used to establish a recommended daily dietary protein intake for a patient, by determining the patient's endogenous nitrogen elimination capacity, calculating an amount of dietary protein that this endogenous capacity permits the patient to process without assistance from a nitrogen scavenging drug, and adding to the amount of dietary protein the patient can process on his/her own an amount of protein that the patient would be able to process when using a particular dosage of PBA or a PBA prodrug like HPN-100. Using HPN-100 as an example, a maximum daily dosage of about 19 grams of HPN-100, utilized at an estimated efficiency of 60%, would enable the treated patient to eliminate waste nitrogen corresponding to about 40 g of dietary protein. Thus the invention provides a method to establish a suitable dietary protein level for a patient having a urea cycle disorder or HE, by adding this amount of protein to the amount the patient's endogenous nitrogen elimination capacity can handle.

In some embodiments, it is also useful to measure PAGN excretion, which accounts for some of the total waste nitrogen excreted when PAA or a PAA prodrug is working. The total waste nitrogen excreted minus the amount of PAGN excreted represents the patient's endogenous capacity for excreting nitrogen wastes via the urea cycle or other mechanisms, and is helpful in determining how much protein intake the patient can manage at a given drug dosage, and also for understanding whether the patient requires extremely close monitoring. The endogenous capacity to excrete nitrogen wastes will be very patient-specific. Dosage of HPN-100 can then be established by determining the subject's endogenous capacity to eliminate waste nitrogen; subtracting the amount of dietary protein corresponding to the subject's endogenous nitrogen elimination capacity; and providing a dosage of HPN-100 sufficient to permit the subject to handle the balance of waste nitrogen, based on the subject's dietary protein intake.

The plasma or blood level of ammonia is optionally also determined, in addition to measuring urinary PAGN, to assess the effectiveness of the overall drug and dietary regimen for a particular patient. If the ammonia control is inadequate, the dosage of the nitrogen scavenging drug may need to be increased if that can be done, or the patient's dietary protein intake can be decreased if that is feasible.

In some instances, the dosage of HPN-100 may be limited to dosages that do not exceed recommended dosing levels for phenylbutyrate, adjusting for the fact that each mole of HPN-100 can produces three moles of phenylbutyrate. The label for the use of sodium PBA for the chronic treatment of UCDs recommends a daily dosage not to exceed 20 g; a daily dosage in a range of 9.9-13.0 g/m$^2$ set according to the subject's size for subjects over 20 kg in weight; and a dosage within a range of 450-600 mg/kg for subjects weighing less than or equal to 20 kg is indicated. While lower doses of HPN-100 may provide comparable ammonia scavenging to PBA on a molar equivalent basis, it may be suitable to select a higher dosage of HPN-100 to achieve adequate ammonia control for certain subjects. Typically, that dose will not exceed the recommended ranges for dosages of phenylbutyrate for a given indication. Thus it may be appropriate to administer HPN-100 at a daily dosage not to exceed an amount of HPN-100 that corresponds to the molar amounts of phenylbutyrate described above (and correcting for the fact that HPN-100 can provide three molecules of PBA). For a subject weighing more than 20 kg, a dosage range for HPN-100 would be between 8.6 and 11.2 mL/m$^2$. For a subject weighing less than 20 kg, a dosage range of about 390 to 520 µL/kg per day of HPN-100 would be appropriate, based on the use of an equimolar amount compared to the recommended doses of HPN-100. There is no evidence to suggest that HPN-100 would produce adverse effects at a rate in excess of that from an equimolar amount of sodium PBA, so the daily recommended upper limit of 20 g per day of sodium PBA suggests that a daily dose limit of HPN-100 based on the recommendations for sodium PBA would correspond to an equimolar amount of HPN-100, or about 19 g or 17.4 mL.

Thus in one embodiment, the invention provides a method to monitor the effectiveness of a treatment of a UCD patient with HPN-100, where monitoring consists of, or consists essentially of, monitoring the patient's urinary PAGN excretion and/or plasma ammonia levels. Urinary PAGN levels comparable to those achieved with a previous PBA dosing regimen would be considered evidence that the HPN-100 treatment was equally effective as the PBA treatment it replaced. Alternatively, a plasma ammonia level that was normal, e.g., a level of less than about 40 µmol/L, or of not greater than 35 µmol/L, would indicate the treatment was effective. In some embodiments, rather than using urinary PAGN output measured over time, one can use the ratio of PAGN to creatinine in the urine, in a spot test.

However, it has also been found that HPN-100 exhibits no indications of toxicity at equimolar doses when compared to the approved PBA dosage of 20 g/day and a dose 2-3 times the equivalent of 20 grams of PBA is unlikely to produce PAA blood levels leading to AEs. Moreover, tolerability of taking HPN-100 is much higher than for PBA and a linear relationship has been observed between HPN-100 dose and PAGN output up to doses of 17.4 mL. In some patients or clinical settings, HPN-100 doses well above the approved PBA dosage are expected to be beneficial; for example, in UCD patients who exhibit recurrent hyperammonemia even on maximal doses of sodium PBA, in UCD patients who need increased dietary protein to support body requirement, or in patients with other nitrogen retaining states.

Thus in another embodiment, the invention provides methods to treat a subject having HE or UCD, with a dosage of HPN-100 that corresponds to between 100 and 300% of the equimolar amount of the recommended highest dose of PBA. In some embodiments, the suitable dosage will be between about 120% and 180% of the highest recommended dose of PBA; in other embodiments it will be between 120-140% or from 140-160% or from 160-180% of the equimolar amount of the recommended highest dosage of PBA. In accordance with this aspect, the daily dosage of HPN-100 could be as much as 57 g, or up to about 38 g, or up to about 33 g, or up to about 30 g, or up to about 25 g.

In one aspect, the invention provides a method to identify the starting dose or dose range and to individually adjust the dose or dose range of a nitrogen scavenging drug comprising PAA or a PAA prodrug (including HPN-100) used for the management of a treatment-naïve patient, which method comprises the steps of:

a) administering an initial dosage of the drug estimated according to the patient's dietary protein load, taking into account the expected percentage conversion to PAGN b) measuring the amount of total waste nitrogen excreted following administration of the nitrogen scavenging drug comprising PAA or a PAA prodrug;

c) measuring blood ammonia to determine if the increase in urinary excretion of total waste nitrogen is sufficient to control blood ammonia levels; and d) adjusting the initial dosage to provide an adjusted dosage of the nitrogen scavenging drug comprising PAA or a PAA prodrug based upon ammonia control, dietary protein, and the amount of total waste nitrogen excreted by the patient, or the amount of waste PAGN excreted. Either or each of these parameters can be monitored to assess the dosage of HPN-100 or other nitrogen scavenging drug being administered. Optionally, the method also includes determining the subject's endogenous nitrogen eliminating capacity (residual urea synthesis capacity) to further help determine an initial dose of HPN-100.

The initial dosage of the HPN-100 for a treatment naïve patient can be calculated as the amount of waste nitrogen that needs to be eliminated based on the patient's dietary protein intake. This amount can be reduced by an amount equivalent to the waste nitrogen the patient can eliminate using the patient's endogenous waste nitrogen elimination capacity, which can be measured as described herein. The suitable starting dose of HPN-100 can be calculated by estimating dietary protein intake that needs to be managed via the nitrogen scavenging drug, and providing a dose of drug amounting to about 1 g of HPN-100 per 1-2 grams of dietary protein in excess of the amount the patient's endogenous nitrogen elimination capacity can handle, taking into account the expected percentage conversion of the administered PBA to urinary PAGN. The method optionally further includes assessing urinary PAGN output to see if it accounts for the expected amount of waste nitrogen, and optionally may include measuring plasma levels of ammonia in the subject to ensure that an acceptable level of ammonia has been achieved. Checking the patient's plasma ammonia levels provides a measure of the effectiveness of the overall treatment program, including diet and drug dosing.

The table below summarizes the amount of dietary protein that doses of HPN-100 below (dose 1), within (dose 2) and above (dose 3) those corresponding to the recommended dosages of sodium PBA would be expected to 'cover' (i.e. mediate resulting waste nitrogen excretion), given the following assumptions: 1 gram of PAA mediates the excretion of ~0.18 grams of waste nitrogen if completely converted to PAGN; 60% of the PAA delivered as the PBA prodrug released from HPN-100 is converted to PAGN; 47% of dietary protein is excreted as waste nitrogen, and 16% of dietary protein consists of nitrogen (Brusilow 1991; Calloway 1971). These factors can be used when relating dietary protein intake, drug dosing and waste nitrogen elimination for purposes of the present invention.

| HPN-100 Doses and Expected Waste Nitrogen Excretion Based on Dietary Protein | | |
|---|---|---|
| Dose 1 | 3 mL BID | Corresponds to ~0.47x the dose administered in Example 2, for a 70 kg adult and ~0.35x the amount of PBA (~6.1 g) delivered in the maximum approved dose of sodium PBA of 20 g<br>Expected to mediate excretion of waste nitrogen associated with ~8.5 g of dietary protein |
| Dose 2 | 9 mL BID | Corresponds to ~1.42x the dose administered in Example 2, for a 70 kg adult and ~01.1x the amount of PBA (~18.2 g) delivered in the maximum approved dose of sodium PBA of 20 g<br>Expected to mediate excretion of waste nitrogen associated with ~26 g of dietary protein |
| Dose 3 | 15 mL BID | Corresponds to ~2.36x the dose administered in Example 2, for a 70 kg adult and ~1.73 x the amount of PBA (~30.3 g) delivered in the maximum approved dose of sodium PBA of 20 g<br>Expected to mediate excretion of waste nitrogen associated with ~43 g of dietary protein |

As used herein, plasma levels of ammonia are acceptable when they are at or below a level considered normal for the subject, and commonly this would mean plasma ammonia level is below about 40 μmol/L. In certain clinical tests described herein the upper limit of normal for the subjects was between 26 and 35 μmol/L, and it is recognized in the art that a normal ammonia level will vary depending upon exactly how it is measured; thus as used to describe ammonia levels herein, 'about' means the value is approximate, and typically is within ±10% of the stated numeric value.

In other aspects, the invention provides a method to identify a suitable starting dose or dose range for a UCD or HE patient and to individually adjust the dose or dose range of a new nitrogen scavenging drug used for the management of a patient already treated with a previous nitrogen scavenging drug, which method comprises the steps of:

a) administering an initial dosage of the new nitrogen scavenging drug (which can be estimated according to the patient's dietary protein load and/or the dose of the new drug expected to yield the same amount of urinary PAGN excretion as a previously used nitrogen scavenging drug);

b) measuring the amount of total waste nitrogen and/or of PAGN excreted following administration of the new drug;

c) optionally measuring blood ammonia to determine if the initial dosage is sufficient to control blood ammonia levels, or to establish a suitable average ammonia level; and d) adjusting the initial dosage of the new drug as needed to provide an adjusted dosage based upon ammonia control, dietary protein, and the amount of total waste nitrogen excreted by the patient. The adjusting of the initial dosage is done based on the amount of urinary PAGN, without relying upon plasma levels of PAA, PBA, or PAGN, and preferably without relying upon plasma levels of ammonia.

Where the patient has previously been treated with PAA or a PAA prodrug, the treating physician may rely, wholly or in part, upon the previous treatment to set a dosage for a new PAA prodrug, or a PBA prodrug, to be administered to the same patient. If the previous drug was reasonably effective for managing the patient's condition, the physician may set the dosage for a new PAA or PBA prodrug by reference to the previous one, so that the new drug is administered at a dosage that provides the same dosage of PAA to the patient, assuming complete conversion of each prodrug into PAA.

Again, as discussed above, it is sometimes desirable to measure PAGN excreted in addition to total waste nitrogen excreted. The total waste nitrogen excreted minus the amount of PAGN excreted represents the patient's endogenous capacity for excreting nitrogen wastes via urea cycle or other mechanisms, and is helpful in determining how much protein intake the patient can manage at a given drug dosage, and also for understanding whether the patient requires extremely close monitoring. The endogenous capacity to excrete nitrogen wastes will be very patient-specific.

In another aspect, the invention provides a method to identify the amount of dietary protein that could be safely ingested by a subject with a nitrogen accumulation disorder, including hepatic encephalopathy and UCD, where the patient is taking an ammonia-scavenging drug that comprises PAA or a PAA prodrug, which method comprises the steps of:
  a) measuring the amount of total waste nitrogen excreted following administration of the drug,
  b) determining the amount of dietary protein calculated to yield an amount of waste nitrogen less than or equal to urinary waste nitrogen; and
  c) adjusting dietary protein and/or drug dosage as appropriate based upon measurement of blood ammonia and total waste nitrogen excretion.

Where the subject is receiving treatment with a nitrogen-scavenging drug, it may be necessary to reassess the patient's dietary intake of protein periodically, since many factors will affect the balance between nitrogen intake, nitrogen excretion, and dosage of a nitrogen scavenging drug. The invention provides methods to determine how much dietary protein a patient can handle, based on measuring the patient's nitrogen excretion levels. It may further be useful to measure the patient's PAGN level as discussed above, to help determine the patient's endogenous capacity for excreting nitrogen wastes via urea cycle or other mechanisms.

In the above methods, the patient may be one having a urea cycle disorder, or other nitrogen accumulation disorders. In many embodiments, the methods are applicable to patient's having a urea cycle disorder, but relatively normal liver function.

The above methods can be practiced with a variety of prodrugs of PAA or PBA. In some embodiments, HPN-100 is the PBA prodrug of choice for these methods.

In another aspect, the invention provides a method to transition a patient from treatment with an initial amount of phenylacetate or phenylbutyrate to a final amount of a PBA prodrug, comprising:
  a) determining a replacement amount of a PBA prodrug to replace at least a portion of the phenylacetate or phenylbutyrate;
  b) substituting the replacement amount of the prodrug for the portion of phenylacetate or phenylbutyrate; and
  c) monitoring the amount of PAGN excreted by the patient to assess the effectiveness of the replacement amount of the prodrug.

Optionally, this method comprises adjusting the amount of the prodrug and administering an adjusted amount of the prodrug, then further monitoring PAGN excretion to assess the effectiveness of the adjusted amount of the prodrug. The replacement amount of the PBA prodrug can be about an equimolar amount to the amount of PBA being replaced.

For reasons discussed extensively herein, it is misleading to rely upon PAA levels when moving a patient to a prodrug (or a new prodrug) of PAA or PBA. The availability of liver-based mechanisms for rapid conversion of a prodrug into PAGN without necessarily entering the systemic system renders plasma levels of PAA and PBA insufficient as predictors of efficacy, so the method relies upon the excreted PAGN for assessing and monitoring treatment with a PAA or PBA prodrug that is to be given to the patient.

In many cases, it will be possible to transition a patient directly from, e.g., phenylbutyrate to HPN-100 or another PBA prodrug in a single stage, rather than in incremental steps. Thus all of the previously used PAA or PAA prodrug may be replaced with a suitable substitution amount of the new drug (PBA prodrug). However, in some situations (e.g. 'fragile patients', patients taking dosages at or near the recommended limits of PAA or PAA prodrug, and for patients having very limited endogenous capacity for excreting nitrogen wastes, or in situations where the ability of the patient to metabolize or excrete the drug is uncertain), it may be preferable to transition from the initial drug to a new PBA prodrug like HPN-100 in two or more stages or steps. Thus the transition may be made in 2, 3, 4 or 5 steps, and at each step a fraction of the original drug (e.g, about half for a two-step transition, about a third for a three-step transition, etc.) is replaced by the new PBA prodrug to be administered. This approach might be appropriate for a 'fragile' UCD patient known to be susceptible to repeated episodes of hyperammonemia while receiving treatment or while taking a large amount of drug that promotes nitrogen elimination.

Thus in another aspect, the invention provides a method to transition a UCD patient from treatment with an initial amount of phenylacetate or phenylbutyrate to a final amount of a PBA prodrug, comprising:
  a) determining a replacement amount of a PBA prodrug to replace at least a portion of the phenylacetate or phenylbutyrate;
  b) substituting the replacement amount of the prodrug for the phenylacetate or phenylbutyrate; and
  c) monitoring plasma level of ammonia in the patient to assess the effectiveness of the replacement amount of the prodrug.

In some embodiments, the replacement amount of the prodrug is an equimolar amount compared to the amount of PBA being replaced During the monitoring step, the patient is being treated with a mixture of phenylacetate or phenylbutyrate plus the new prodrug. The proportion depends upon what step of the transition the patient is in. The physician can also use information about the effects of a first step in setting the replacement amount of the prodrug for use in subsequent steps; thus if the prodrug is significantly more effective than predicted when the estimated amount used as a replacement amount is administered in a first step, the replacement amount used in a subsequent step of the transition can be proportionally reduced.

In another aspect, the invention provides a method to initiate treatment with phenylacetate, phenylbutyrate or a PBA prodrug in a step-wise fashion, as might be appropriate for a 'fragile patient' (a UCD patient with a history of frequent symptomatic hyperammonemia and/or neonatal onset disease who presumably has no urea synthetic capacity, or a patient with severely compromised liver function whose ability to metabolize the drug may be uncertain). This process may be more complex, since the prodrug will rely upon liver function to be activated and to function; thus the method is preferably done in a stepwise fashion, exemplified by the following steps:

a) estimating or measuring dietary nitrogen intake for the patient; and/or
b) estimating the patient's need for urinary waste nitrogen excretion; then
c) administering a starting dose of the drug estimated to provide a fraction of the necessary waste nitrogen clearance as excreted PAGN; and
d) increasing the dose of drug as appropriate, and repeating the steps above, to reach a maintenance dose of the drug.

The methods also include optionally measuring total urinary nitrogen and urinary PAGN after at least 3 days of drug administration, at which point a steady state has been achieved. It also can include calculating the amount of drug converted to PAGN, which would be expected to be at least 50%, to determine if the drug is having the desired effect. A suitable dosage of the drug would be identified as one where the amount of excreted PAGN is sufficient to clear the expected amount of waste nitrogen from the dietary intake of protein, which can be adjusted to account for the patient's endogenous nitrogen elimination capacity.

The fraction of nitrogen waste to be cleared in a single step can be selected with due regard to the severity of the patient's condition (nitrogen accumulation disorder). In some embodiments, it will be appropriate to target removal of about 50% of the waste nitrogen for which clearance assistance is needed. In some embodiments, the method will target removal of about 100% of the waste nitrogen.

In another aspect, the invention provides a method to transition a patient taking an initial daily dosage of phenylbutyrate from phenylbutyrate to HPN-100, comprising a) determining a suitable amount of HPN-100 to replace at least a portion of the initial daily dosage of phenylbutyrate;
b) administering the suitable amount of HPN-100 to the subject along with an amount of phenylbutyrate corresponding to the initial daily dosage of phenylbutyrate minus an amount corresponding to the portion replaced by HPN-100;
c) determining the level of excreted PAGN for the subject to make sure it has not decreased; and
d) repeating steps a-c until all of the phenylbutyrate is replaced by HPN-100.

If it is found that the amount of excreted PAGN decreases, additional HPN-100 or additional PBA would be administered to reestablish a level of PAGN excretion that is suitable for the patient, and the replacement steps would then be continued until all of the PBA was replaced by HPN-100.

Here again, the portion of phenylbutyrate to be replaced in an initial step can be 100%, about ½, about ⅓, or about ¼, or some value between these. During a stepwise process, where less than all of the phenylbutyrate is replaced in a first step, the patient will receive both HPN-100 and phenylbutyrate. As demonstrated herein, the appropriate method for determining a suitable dose of HPN-100 will take account of the excreted PAGN, rather than being based only on less reliable criteria for evaluating the orally delivered PBA prodrug.

In another embodiment, the invention provides a method to administer a phenylbutyrate prodrug to a patient, comprising determining the rate of PAGN excretion for the subject following administration of at least one phenylbutyrate prodrug, and selecting or adjusting a dose administration schedule based on the PAGN excretion rate. The compound can be a compound of Formula I, Formula II or Formula III as described above. Advantageously, the compounds used herein as prodrugs of PBA achieve nitrogen scavenging comparable to that of PBA but exhibit a slow-release kinetic profile that produces a more stable ammonia level in the treated subject. In some embodiments, the methods of the invention include administering a prodrug as described herein to a subject at a dosage that provides comparable ammonia level control to that achieved by PBA, but with significantly lower exposure of the subject to systemic PBA. In some embodiments, the subject experiences pharmacokinetic parameters for PBA that demonstrate lower exposure to PBA, including a lower AUC and Cmax for PBA, while maintaining a plasma ammonia level comparable to or better than that provided by treatment with a dosage of PBA within the normal dosing range. When HPN-100 and PBA were administered to UCD patients at equimolar dosages, the patient receiving HPN-100 had overall lower plasma ammonia levels, and also lower PBA exposure:

|  | AUC ($NH_3$) μg-hr/mL | $C_{max}$ ($NH_3$) μg-hr/mL | AUC (PBA) μg-hr/mL | $C_{max}$ (PBA) μg-hr/mL |
|---|---|---|---|---|
| PBA | 38.4 (20) | 79.1 (40) | 739 (49) | 141 (44) |
| HPN-100 | 26.1 (10) | 56.3 (28) | 540 (60) | 70 (65) |

While a larger data set is needed to demonstrate statistical significance, limited amounts of data are available in part due to the rarity of these conditions. Nevertheless, the data indicates that PBA treatment resulted in less effective ammonia level control and greater exposure to PBA, while the PBA prodrug HPN-100 at equimolar dosing provided better ammonia level control and lower PBA exposure levels. Accordingly, in one aspect the invention provides a method to treat a UCD patient with a PBA prodrug, wherein the prodrug produces better ammonia level control than PBA without increasing the patient's exposure to PBA as judged by the AUC and Cmax for PBA, when compared to treatment with an equimolar amount of PBA. In some embodiments, the treatment uses HPN-100 as the prodrug, and in some embodiments the AUC for PBA exposure is lower with the prodrug than with PBA by at least about 20%; or the exposure to PBA upon treatment with the prodrug is lower by at least about 30% compared to treatment with PBA; or both of these conditions are met to demonstrate reduced exposure to PBA. In some embodiments, the AUC for PBA is less than about 600 and the Cmax for PBA is less than about 100 when the prodrug is administered. Preferably, the prodrug provides plasma ammonia levels that average less than about 40 μmol/L or not more than 35 μmol/L.

The advantageous slow-release kinetic profile of compounds used herein as prodrugs of PBA permits less frequent and more flexible dosing in selected patients as compared with sodium PBA. While all patients with UCDs and a propensity for elevated ammonia levels should in principle be able to benefit from the ammonia scavenging activity of HPN-100, UCD patients with substantial residual urea synthetic capacity (e.g. UCD whose first manifestations occur at several years of age or older; i.e. patients who do not exhibit neonatal onset) would be the best candidates for three times daily or even twice daily dosing with PBA prodrugs such as HPN-100. Patients with cirrhosis and HE would also be candidates for less frequent dosing, as even patients with severe liver disease have significant residual urea synthetic capacity (Rudman et al., *J. Clin. Invest.* 1973).

Specific embodiments of the invention include the following:

A. A method to determine an effective dosage of HPN-100 for a patient in need of treatment for a nitrogen retention disorder, which comprises monitoring the effect of an initial dosage of HPN-100, wherein monitoring the effect consists essentially of determining the patient's urinary phenylacetyl glutamine (PAGN) output.

In this method, the initial dose for a treatment-naïve patient would take into account the expected percentage conversion of the administered PBA to urinary PAGN, and urinary PAGN output can be determined as a ratio of urinary PAGN to urinary creatinine, since it has been demonstrated by others that creatinine, the daily excretion of which tends to be constant for a given individual, can be used as a means to normalize measures of urinary parameters while correcting for variations in urinary volume. In these methods, the nitrogen retention disorder can be chronic hepatic encephalopathy or a urea cycle disorder. Plasma ammonia levels may also be monitored to adjust the overall treatment program and dietary protein intake, but as discussed above, urinary PAGN provides a preferred way to assess the drug's role in waste nitrogen elimination.

B. A method to determine an effective dosage of HPN-100 for a patient in need of treatment for a nitrogen retention disorder, which comprises monitoring the effect of an initial dosage of HPN-100, wherein the initial dose for a treatment-naïve patient would take into account the expected percentage conversion of the administered PBA to urinary PAGN, and wherein monitoring the effect of the initial dosage of HPN-100 consists essentially of determining the patient's urinary phenylacetyl glutamine (PAGN) output and/or total urinary nitrogen. In these methods, administering the effective dosage of HPN-100 to the patient preferably produces a normal plasma ammonia level in the patient. This can be a level of about 35 or about 40 µmol/L.

C. A method to determine a starting dosage of HPN-100 for a patient having a nitrogen retention disorder, which comprises calculating the dosage of HPN-100 based on a utilization efficiency of about 60% to about 75%. In such methods, the dosage of HPN-100 can be calculated from the patient's dietary protein intake, or it can be estimated from the patient's body weight and approximate growth rate. In such methods, the dosage of HPN-100 is sometimes reduced to account for the patient's residual urea synthesis capacity, by adjusting the amount of HPN-100 to reflect the amount of ammonia scavenging needed in view of the patient's endogenous capacity for nitrogen elimination.

D. A method to determine a dosage of a PAA prodrug for a patient having a nitrogen retention disorder, comprising:
 a) determining the patient's residual urea synthesis capacity;
 b) determining the patient's dietary protein intake;
 c) estimating from a) and b) the patient's target urinary PAGN output;
 d) determining an amount of the PAA prodrug needed to mobilize the target amount of urinary PAGN based on about 60% to about 75% conversion of the PAA prodrug into urinary PAGN.

In these methods, the PAA prodrug can be phenylbutyric acid (PBA) or a pharmaceutically acceptable salt thereof, or it can be HPN-100.

E. A method to treat a patient having an ammonia retention disorder with a suitable dosage of a PAA prodrug, comprising:
 a) determining the patient's residual urea synthesis capacity;
 b) determining the patient's dietary protein intake;
 c) estimating from a) and b) the patient's target urinary PAGN output;
 d) determining an amount of the PAA prodrug needed to mobilize the target amount of urinary PAGN based on about 60% to about 75% conversion of the PAA prodrug into urinary PAGN; and
 e) administering to the patient the suitable dosage of the PAA prodrug.

In these methods, the PAA prodrug is often phenylbutyrate or a pharmaceutically acceptable salt thereof, or HPN-100.

G. A method to transition a patient receiving treatment with an initial amount of phenylacetate or phenylbutyrate to a final amount of HPN-100, comprising:
 a) determining a replacement amount of HPN-100 to replace at least a portion of the phenylacetate or phenylbutyrate;
 b) substituting the replacement amount of the HPN-100 for the phenylacetate or phenylbutyrate; and
 c) monitoring the amount of urinary PAGN excreted by the patient to assess the effectiveness of the replacement amount of the HPN-100.

In these methods, an increase the amount of urinary PAGN may indicate that the amount of HPN-100 can be reduced, and a decrease in urinary PAGN may indicate the amount of HPN-100 needs to be increased.

H. A method to transition a patient taking an initial daily dosage of phenylbutyrate from phenylbutyrate to HPN-100, comprising
 a) determining a suitable amount of HPN-100 to replace at least a portion of the initial daily dosage of phenylbutyrate;
 b) administering the suitable amount of HPN-100 to the subject along with an amount of phenylbutyrate corresponding to the initial daily dosage of phenylbutyrate minus an amount corresponding to the portion replaced by HPN-100;
 c) determining the level of excreted urinary PAGN for the subject; and
 d) repeating steps a-c until all of the phenylbutyrate is replaced by HPN-100.

I. A method to initiate treatment with phenylacetate, phenylbutyrate or a HPN-100 in a step-wise fashion, comprising:
 a) estimating or measuring dietary nitrogen intake for the patient; and/or
 b) estimating the patient's need for urinary waste nitrogen excretion based upon diet and urea synthetic capacity; then
 c) administering a starting dose of the drug estimated to provide a fraction of the necessary waste nitrogen clearance as urinary PAGN taking into account the expected percentage conversion of the administered PBA to urinary PAGN; and
 d) increasing the dose of drug as appropriate, and repeating the steps above, to reach a maintenance dose of the drug.

J. A method to treat a UCD patient with a PBA prodrug, wherein the prodrug produces equivalent or better ammonia level control compared to PBA without increasing the patient's exposure to PBA as judged by the AUC and Cmax for PBA when the patient receives the PBA prodrug, when compared to the AUC and Cmax observed when the patient receives an equimolar amount of PBA.

In these methods, the PBA prodrug is often HPN-100.

The methods include a method to treat a patient having a nitrogen retention disorder with the PBA prodrug HPN-100, wherein the AUC for PBA exposure can be lower with the prodrug than with PBA by at least about 20%, or by at least about 30% compared to treatment with PBA. This is believed to be related to the slow absorption or uptake characteristics of HPN-100, which provide a more stable level of PBA exposure and provide an unexpected advantage of HPN-100 to be effective with less frequent dosing when compared to sodium phenylbutyrate.

K. A method to determine a suitable dietary protein level for a patient having a nitrogen retention disorder, comprising:
- a) determining the patient's endogenous nitrogen elimination capacity;
- b) calculating from the endogenous nitrogen elimination capacity an amount of dietary protein the patient can process without the aid of a nitrogen scavenging drug;
- c) then adding an amount of protein that the patient should be able to process with the assistance of selected dosage of a nitrogen scavenging drug to arrive at an amount of dietary protein the patient can have while being treated with the selected dosage of the nitrogen scavenging drug, taking into account the amount of protein required for health and body growth.

In this method, the nitrogen scavenging drug can be HPN-100. Commonly, the selected dosage of HPN-100 is not more than about 19 grams per day, and the amount of dietary protein the patient should be able to process with the assistance of this amount of HPN-100 is about 1 grams (~1.3 g) of protein per gram of HPN-100.

L. A method to treat a patient with a PBA prodrug, comprising administering HPN-100 at a daily dose in excess of 19 g per day to a subject having HE or UCD. Optionally, the daily dose of HPN-100 is between about 20 g and about 57 g.

M. A method for determining the dosing schedule of a PBA prodrug wherein the patient retains substantial residual urea synthetic capacity, as would be the case for most patients with cirrhosis and HE or most UCD patients who do not exhibit symptoms within the first two years of life.

In the foregoing methods that utilize HPN-100, the exposure to PBA upon treatment with the prodrug HPN-100 is lower by at least about 30% compared to treatment with PBA. Also, commonly the AUC for PBA is less than about 600 and the Cmax for PBA is less than about 100 when the prodrug is administered. Also, in the foregoing methods, when the subject is treated with the prodrug, which can be HPN-100, the subject will typically achieve and maintain normal plasma ammonia levels.

The following examples are offered to illustrate but not to limit the invention.

The data below from three human studies and one preclinical study illustrate that the conventional approach of assessing drug exposure and effect by measuring blood levels does not correlate with nitrogen scavenging as assessed by urinary excretion of PAGN or by reduction of plasma ammonia. These data demonstrate that, surprisingly, the plasma level of PBA or PAA seen with an effective amount of a prodrug can be far less the plasma level of PBA or PAA seen with a similarly effective amount of phenylbutyrate. Moreover, they demonstrate the need to allow for incomplete conversion of sodium PBA or HPN-100 into PAGN in selecting starting dosage, the delayed release behavior and implications for dosing schedule of delivering PBA as a triglyceride rather than as a salt, and the possibility of administering HPN-100 in doses greater than those currently recommended for sodium PBA. These are followed by a biological explanation for the findings.

Example 1

Single Dose Safety and PK in Healthy Adults

To assess its pharmacokinetic (PK) and pharmacodynamic (PD) profile, HPN-100 was administered as a single dose to 24 healthy adults. Pharmacokinetic samples were taken pre-dose and at 15 and 30 minutes post-dose and 1, 1.5, 2, 3, 4, 6, 8, 12, 24, and 48 hours post-dose. As discussed below, plasma levels of the major HPN-100 metabolites PBA, PAA and PAGN were many fold lower after administration of HPN-100 than after sodium PBA. By contrast, urinary excretion of PAGN was similar between the two groups (4905+/−1414 mg following sodium PBA and 4130+/−925 mg following HPN-100) and the differences that were observed were determined to be largely an artifact of incomplete collection due to stopping urine collection at 24 hours (note that PAGN excretion following administration of sodium PBA was largely complete at 24 hours but continued beyond 24 hours following administration of HPN-100). Thus, the plasma metabolite concentrations did not accurately reflect the comparative ammonia scavenging activity of sodium PBA and HPN-100.

Three healthy adult volunteers were treated with a single dose of either sodium PBA or HPN-100 at a dosage of 3 $g/m^2$. Plasma levels of PAA, PBA, and PAGN were monitored periodically for 12-24 hours by known methods. Results of this are shown in FIG. 4, which shows a curve for each subject (note the log scale).

In each panel, the curves represent measured levels of PBA, PAA or PAGN in subjects receiving sodium PBA at 3 $g/m^2$ dosage, or HPN-100 in an amount calculated to provide an equimolar amount of PBA to that provided by the sodium PBA dosage. Three curves for each material are for three subjects who received the specified dosages of sodium PBA or HPN-100.

In the left panel, the upper curve represents PBA levels; the intermediate one represents PAA levels; and the lowest of the three sets of lines represents PAGN levels. In the right panel, the three lowest curves at the 10-15 hour time span are all for PBA; and the highest three curves at 15-25 hours represent PAGN levels. PAA levels were not determined after approximately 12 hours, and were generally close to the PAGN curves up to that time.

Example 2

Administration of HPN-100 to Patients with Liver Disease

To determine its pharmacokinetic (PK) and pharmacodynamic (PD) profile in patients with liver disease, clinical testing was conducted in which HPN-100 was administered orally as a single dose (100 mg/kg/day on day 1), and twice daily for 7 consecutive days (200 mg/kg/day on days 8 through 14, in two doses of 100 mg/kg per dose), to subjects with hepatic impairment with cirrhosis (Child-Pugh scores of A, B, or C) and to a gender and age-matched control group of healthy adults with normal hepatic function. On day 15, subjects received a single dose of HPN-100 (100 mg/kg). PK blood samples were taken pre-dose, at 15 and 30 minutes post-dose, and at 1, 1.5, 2, 3, 4, 6, 8, 12, and 24 hours post-dose on days 1, 8, and 15, and at 48 hours after dosing on days 1 and 15. On days 9-14, blood samples were taken pre-morning dose and at 2 hours post-morning dose. Urine was collected 0-4, 4-8, 8-12, and 12-24 hours post-dose on days 1, 8, and 15, and at 24-48 hours post-dose on days 1 and 15.

HPN-100 was metabolized via the predominant pathway in all subject groups, and the alternative HPN-100 metabolites PAG (phenylacetyl glycine), PBG (phenylbutyryl glycine), and PBGN (phenylbutyryl glutamine) were below the limit of quantification in all plasma samples. Both the extent of systemic exposure ($AUC_{0-t}$) and $C_{max}$ for PBA and PAA tended to be higher in Child-Pugh group B or C than in Child-Pugh group A or the healthy volunteer group, although there were no significant differences in these variables on day 15. As described below, plasma PAA levels did correlate with Childs-Pugh classification (i.e. were higher in patients with more severe liver disease). However, the average conversion of HPN-100 to PAGN was ~75%, and no difference were seen between patients with cirrhosis and normal healthy volunteers, demonstrating that hepatic impairment did not affect the subjects' ability to activate the PBA prodrug HPN-100 or to utilize it for elimination of excess ammonia. Thus, as summarized in more detail below, plasma metabolite levels did not correlate well with the HPN-100 dosage and, just as for healthy adults, plasma metabolite levels did not accurately reflect the nitrogen scavenging effect of HPN-100. Moreover, the mean conversion of administered PAA to PAGN averaged ~75% in this patient population.

| Analyte | Subject group | Geometric mean ratio | 90% CI | P value for group effect |
|---|---|---|---|---|
| PBA | $AUC_{0-t}$ | | | 0.40 |
| | Child-Pugh A | 0.92 | 0.58-1.43 | |
| | Child-Pugh B | 1.26 | 0.80-1.97 | |
| | Child-Pugh C | 1.37 | 0.87-2.14 | |
| PBA | $C_{max}$ | | | 0.52 |
| | Child-Pugh A | 1.42 | 0.87-2.31 | |
| | Child-Pugh B | 1.35 | 0.83-2.21 | |
| | Child-Pugh C | 1.50 | 0.92-2.45 | |
| PAA | $AUC_{0-t}$ | | | 0.64 |
| | Child-Pugh A | 1.22 | 0.48-3.06 | |
| | Child-Pugh B | 1.53 | 0.61-3.85 | |
| | Child-Pugh C | 1.94 | 0.77-4.88 | |
| PAA | $C_{max}$ | | | 0.72 |
| | Child-Pugh A | 1.33 | 0.70-2.52 | |
| | Child-Pugh B | 1.16 | 0.61-2.20 | |
| | Child-Pugh C | 1.52 | 0.80-2.88 | |

$AUC_{0-t}$, area under the plasma concentration curve from time 0 to the last measurable concentration;
CI, confidence interval;
$C_{max}$, maximum observed plasma concentration;
PAA, phenylacetic acid;
PBA, phenylbutyric acid.

During multiple dosing (days 8-15), there was a trend for higher systemic concentrations of PBA and PAA in subjects with greater hepatic impairment (Child-Pugh B or C) compared with Child-Pugh group A and the healthy volunteers. Unlike PBA, PAA did accumulate significantly in plasma during multiday dosing. Differences between single (day 8) and multiple dosing (day 15: steady state) were significant for $AUC_{0-12}$ and $C_{max}$ of PAA for all subjects combined ($p<0.001$), but not for PBA. After dosing on day 15, extent of exposure to PAA, but not PBA, significantly correlated with hepatic impairment.

The clinical efficacy of HPN-100 is dependent on its ammonia scavenging capabilities, through conjugation of glutamine with PAA to form PAGN. After dosing on each day, PAGN was the major metabolite excreted: 42-49% of the HPN-100 dose administered was excreted as PAGN on day 1, 25-45% on day 8, and 58-85% on day 15. Very low amounts of PBA and PAA were excreted in the urine (≤0.05% of the total HPN-100 dose). There were no significant differences in the amount of PAGN excreted between any of the Child-Pugh groups and the healthy volunteers. Urinary PAGN excretion is also an indication of the ammonia-scavenging capacity of HPN-100, as 2 moles of ammonia combine with 1 mole of PAA to produce PAGN. Hepatic impairment had no significant effect on the ammonia-scavenging ability of HPN-100 in this study. There were no significant differences in the amount of PAGN excreted between any of the Child-Pugh groups and the healthy volunteers. The observations that hepatic impairment had no significant effect on the ammonia-scavenging ability of HPN-100 in this study but was associated with accumulation of PAA in plasma underscores the importance of utilizing urinary PAGN rather than metabolite blood levels to guide drug effect and, as a corollary, the importance of the invention, as does the fact that the mean percentage conversion of administered PAA into urinary PAGN among the 4 treatment groups was ~75%.

Urinary PAGN Excretion After Dosing on Day 15 (0-48 Hours).

| | Child-Pugh A (8) | Child-Pugh B (8) | Child-Pugh C (8) | Healthy Adults (8) |
|---|---|---|---|---|
| Amount excreted (μmol) | | | | |
| Mean (SD) | 31431 (15291) | 25152 (11426) | 30752 (20860) | 28716 (8223) |
| Range | 16016-65229 | 13643-41635 | 6331-60139 | 17203-41092 |
| Molar % of dose excreted | | | | |
| Mean (SD) | 79.6 (30.5) | 58.2 (29.2) | 85.0 (65.1) | 68.6 (21.9) |
| Range | 48.9-138.2 | 26.5-99.6 | 23.1-221.1 | 30.6-96. |
| Molar % of dose ammonia scavenged | | | | |
| Mean (SD) | 159.2 (60.9) | 116.3 (58.3) | 169.9 (130.1) | 137.2 (43.9) |
| Range | 97.9-276.4 | 53.0-199.2 | 46.3-442.3 | 61.3-193.4 |

Of particular note, there was no relationship between the plasma levels of PBA and PAA, which exhibited a non-statistically significant directional change toward higher plasma levels in patients with liver disease than healthy adults, and urinary excretion of PAGN.

Example 3

Administration of HPN-100 to Adults with UCDs

To further explore its pharmacokinetic (PK) and pharmacodynamic (PD) profile in clinical states associated with nitrogen retention, 10 adult UCD patients were switched from sodium PBA to a PBA equimolar dose of HPN-100. Subjects were required to be on a stable dose of sodium PBA before enrolment. Upon enrolment, all subjects received sodium PBA for 7 days and were then admitted to a study unit (Visit 2-1) for overnight observation and 24-hour PK and ammonia measurements and urine collections. Subjects were then converted to the PBA equimolar dose of HPN-100, either in a single step or in multiple steps depending on the total dose of sodium PBA; 9 out of 10 patients converted in a single step. Subjects stayed on the 100% HPN-100 dose for one week and were then re-admitted to the study unit for repeated PK (Visit 11-1), ammonia and urine collections.

The findings from this study, summarized in detail below, demonstrate that, just as in healthy adults and patients with liver disease, plasma metabolite levels do not correlate well with ammonia scavenging activity as reflected by urinary PAGN excretion and corroborated by plasma ammonia results. Moreover, the findings demonstrate considerable inter-individual variability in the percentage of both sodium PBA and HPN-100 that is converted to urinary PAGN.

Pharmacokinetic, ammonia and safety analyses: As summarized in the table below, 7 days of HPN-100 administration resulted in comparable PAA and plasma PAGN levels but slightly lower PBA levels compared to the PBA molar equivalent dose of sodium PBA.

Comparison of Pharmacokinetic Parameters at Steady State - sodium PBA vs. HPN-100

| PK Parameter | Arithmetic Mean (CV %) | |
| --- | --- | --- |
| | Sodium PBA (N = 10) | HPN-100 (N = 10) |
| PBA in Plasma | | |
| $AUC_{0-24}$ (μg·h/mL) | 739 (49.2) | 540 (60.1) |
| $Cmax_{ss}$ (μg/mL) | 141 (44.3) | 70.1 (64.7) |
| $Cmin_{ss}$ (μg/mL) | 0.588 (255) | 2.87 (265) |
| PAA in Plasma | | |
| $AUC_{0-24}$ (μg·h/mL) | 595.6 (123.9) | 574.6 (168.9) |
| $Cmax_{ss}$ (μg/mL) | 53.0 (94.7) | 40.5 (147.6) |
| $Cmin_{ss}$ (μg/mL) | 3.56 (194.4) | 7.06 (310.7) |
| PAGN in Plasma | | |
| $AUC_{0-24}$ (μg·h/mL) | 1133 (31.1) | 1098 (44.2) |
| $Cmax_{ss}$ (μg/mL) | 83.3 (25.8) | 71.9 (56.0) |
| $Cmin_{ss}$ (μg/mL) | 16.8 (86.1) | 12.1 (134.4) |

$AUC_{0-24}$: Area under the concentration from time 0 (pre-dose) to 24 hours,
$Cmax_{ss}$: Maximum plasma concentration at steady state,
$Cmin_{ss}$: Minimum plasma concentration at steady state,
$A_e$: Amount excreted over 24 hours
[1]The mean (SD) sodium PBA dose = 12.6 (4.11) g; the mean (SD) HPN-100 dose = 12.3 (3.91) g.

Despite dissimilar PBA blood levels, overall urinary excretion of PAGN was similar for the two treatments as summarized in the table below. Importantly, and in contrast to the assumptions inherent in current treatment guidelines that all administered sodium PBA is converted to urinary PAGN, considerable inter-individual variability was observed in the percentage of administered PAA converted to PAGN, which averaged ~60% and similar both sodium PBA and HPN-100. Moreover, the 24 hour pattern of excretion appeared to differ in that urine output of PAGN reached its highest level during the 'afternoon hours' (6-12 hour urine collection) for patients treated with sodium PBA, whereas peak output of PAGN occurred overnight (12-24 hour urine collection) for patients on HPN-100 treatment. This difference presumably reflects the slow release characteristics and longer duration of effective blood concentrations of PAA following administration of HPN-100 as compared with sodium PBA. HPN-100 was either not detectable or below the limits of quantitation in all blood samples.

Comparison of Mean PAGN Amount Excreted (μg)—Sodium PBA (Sodium phenylbutyrate) vs. HPN-100

| Treatment | PAGN 0-6 hours | PAGN 0-12 hours | PAGN 12-24 hours | Total PAGN Excretion (CV %) |
| --- | --- | --- | --- | --- |
| sodium PBA | 2,452,838 | 4,859,121 | 4,645,447 | 12,153,473 (48.2) |
| HPN-100 | 2,381,371 | 3,027,310 | 5,433,033 | 10,784,747 (25.9) |

Figure 10:
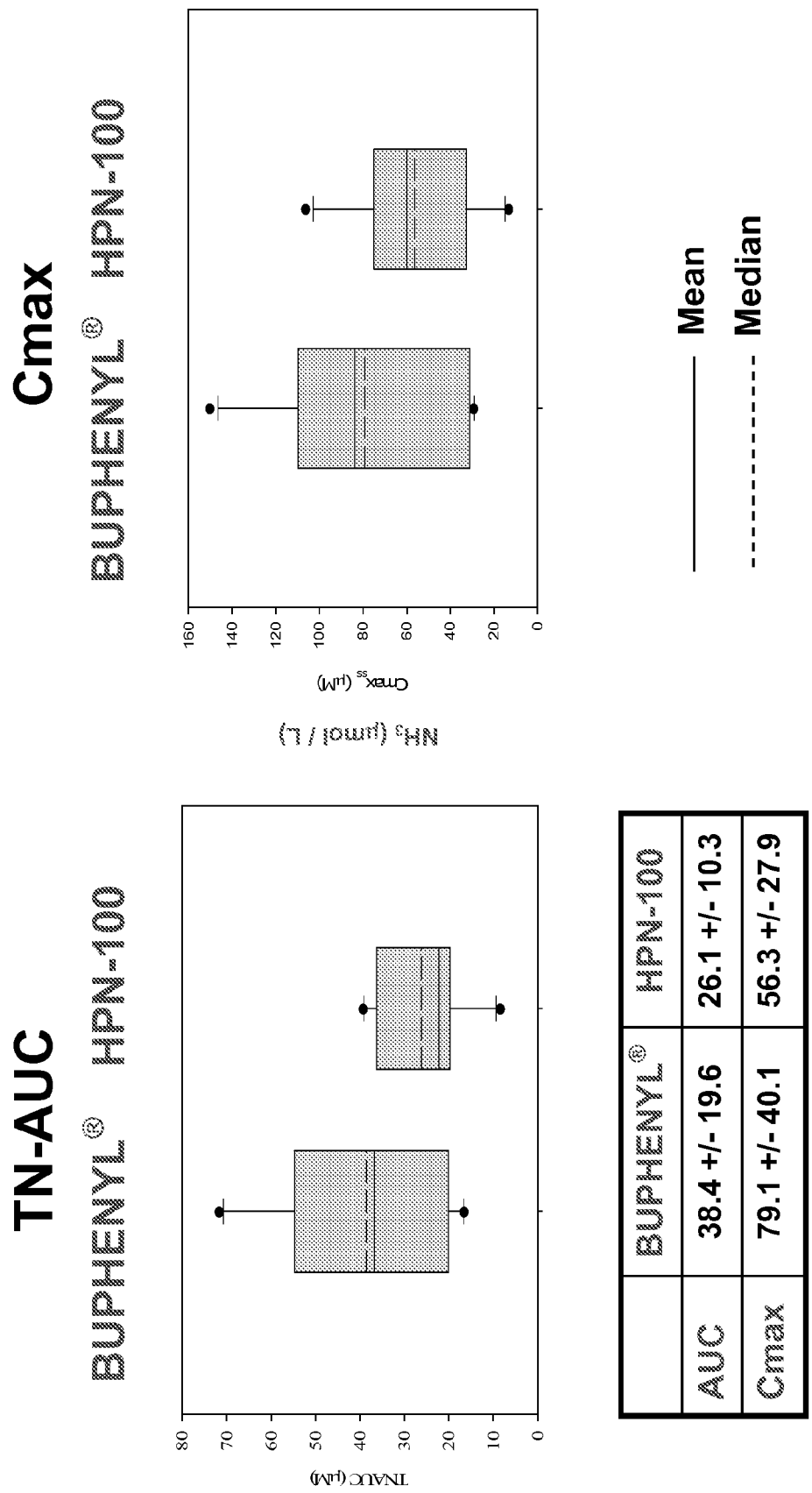
FIG. 10 shows plasma ammonia levels [time-normalized area under the curve, or TN-AUC or Area under the curve (AUC)] during the day and night for 10 UCD patients treated for seven days with either sodium PBA or an equimolar dosage of HPN-100, and illustrates that HPN-100 provided better control of ammonia levels than PBA: both the AUC (area under the curve), which is an index of total ammonia exposure, and Cmax, which measures the peak concentration of ammonia, were lower in subjects receiving HPN-100 than in subjects receiving an equimolar dosage of PBA.

As summarized in the table below, mean time normalized area under the curve (TN-AUC) values for venous ammonia following HPN-100 were directionally (~31%) lower than those observed with sodium PBA (26.1 vs. 38.4 μmol/L) although the differences did not achieve statistical significance (FIG. 10). Likewise, peak venous ammonia concentrations following HPN-100 were directionally (~29%; not statistically significant) lower than those observed with sodium PBA (56.3 vs. 79.1 μmol/L, respectively).

Figure 12:
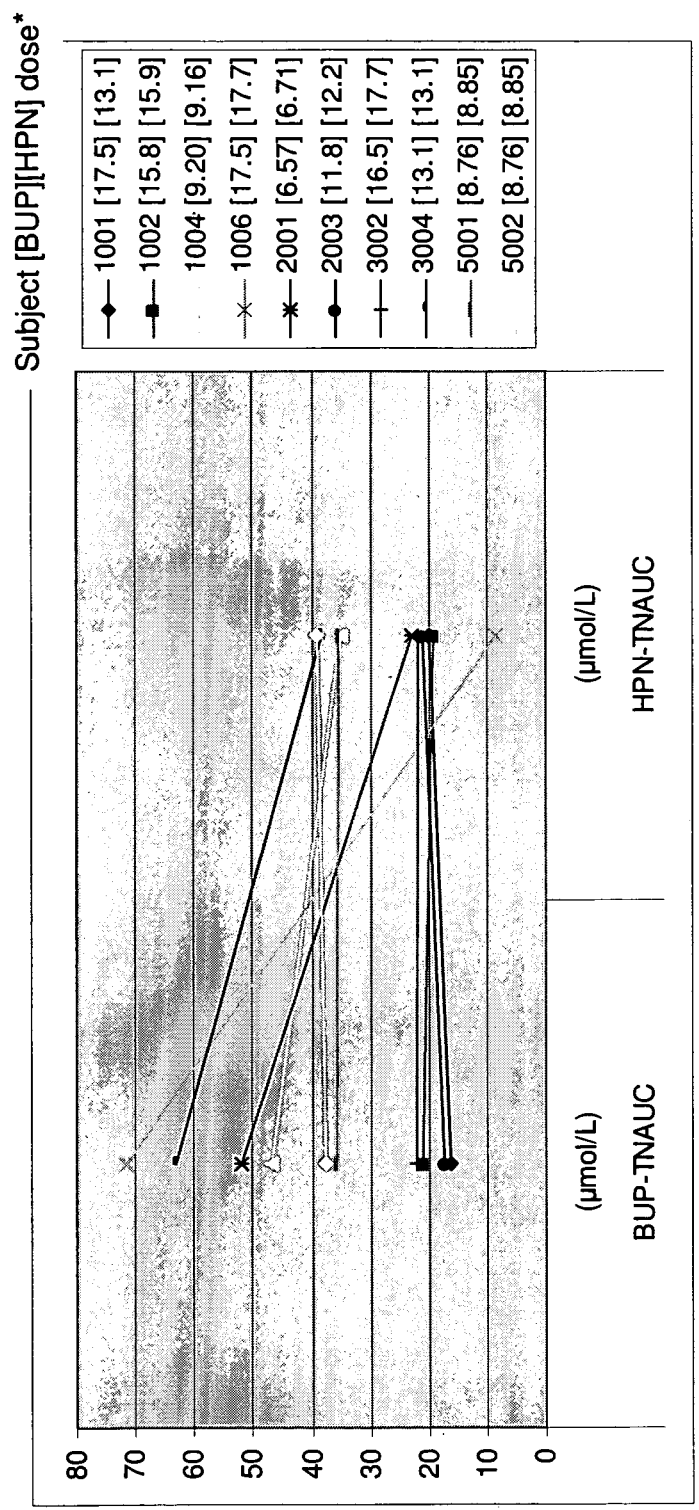
FIG. 12 demonstrates that in patients whose ammonia levels were well controlled on sodium PBA, HPN-100 maintained control. By contrast, patients whose ammonia levels were elevated despite treatment with sodium PBA exhibited the greatest benefit in terms of improved ammonia control from HPN-100.
Figure 13:
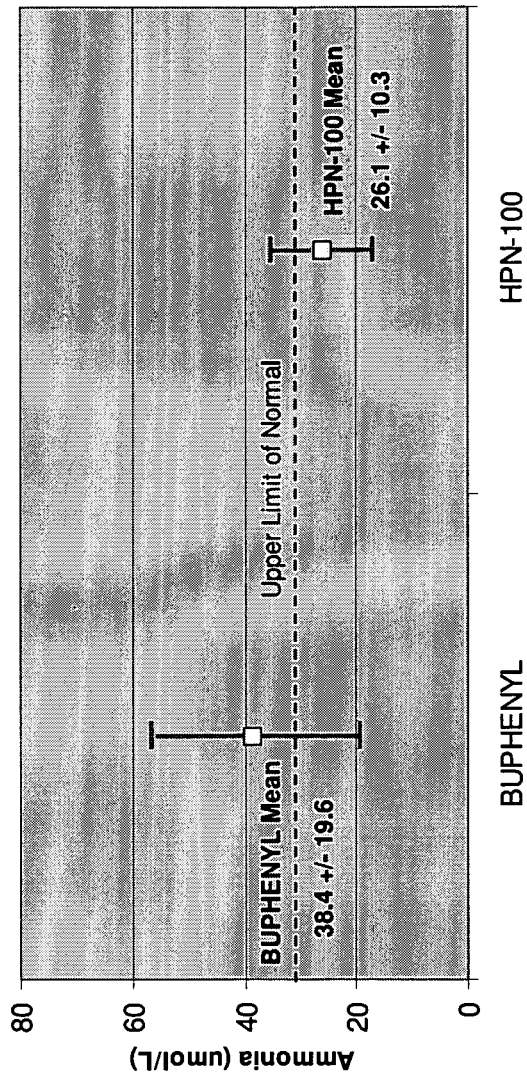
FIG. 13 summarizes the data from FIG. 12 and provides a statistical comparison of ammonia levels for patients on sodium PBA and those on HPN-100. It also shows the normal range for each set of patients.

The normal upper limit for venous ammonia varied among the study sites from 26 to 35 μmol/L. Examination of ammonia values (TN-AUC) for individual patients demonstrated that patients with higher ammonia levels on sodium PBA exhibited greater decreases in ammonia values following administration of HPN-100 (FIG. 12). Moreover, the mean ammonia value after HPN-100 (26.1 μmol/L) was within the normal range while it was above the upper limit of normal (ULN) after sodium PBA (sodium phenylbutyrate) (38.4 μmol/L) (FIG. 13). Likewise the mean percentage of normal ammonia values increased from 58% after sodium PBA treatment to 83% after HPN-100 treatment.

Venous Ammonia Pharmacodynamics Following Seven Days of
Dosing With Either Sodium PBA or HPN-100 (Steady State)

| | Sodium PBA | | | HPN-100 | | |
|---|---|---|---|---|---|---|
| Subject | $Cmax_{ss}$ (µmol/L) | TN-AUC (µmol/L) | PBA Equivalent dose[1] | $Cmax_{ss}$ (µmol/L) | TN-AUC (µmol/L) | PBA Equivalent dose[1] |
| 1001 | 29.0 | 16.47 | 17.5 | 63.0 | 19.8 | 13.1 |
| 1002 | 31.0 | 20.9 | 15.8 | 31.0 | 19.3 | 15.9 |
| 1004 | 85.0 | 46.8 | 99.2 | 106 | 35.1 | 9.16 |
| 1006 | 150 | 71.5 | 17.5 | 13.0 | 8.30 | 17.7 |
| 2001 | 88.0 | 52.1 | 6.57 | 33.0 | 22.7 | 6.71 |
| 2003 | 31.0 | 17.5 | 11.8 | 74.0 | 21.1 | 12.2 |
| 3002 | 108 | 22.3 | 16.5 | 36.0 | 21.9 | 17.7 |
| 3004 | 115 | 62.9 | 13.1 | 75.0 | 38.4 | 13.1 |
| 5001 | 82.2 | 35.8 | 8.76 | 57.0 | 35.5 | 8.85 |
| 5002 | 72.2 | 37.7 | 8.76 | 75.2 | 39.1 | 8.85 |
| N | 10 | 10 | 10 | 10 | 10 | 10 |
| Mean | 79.1 | 38.4 | 12.6 | 56.3 | 26.1 | 12.3 |
| SD | 40.1 | 19.6 | 4.11 | 27.9 | 10.3 | 3.91 |
| Median | 83.6 | 36.8 | 12.5 | 60.0 | 22.3 | 12.7 |
| Min | 29.0 | 16.4 | 6.57 | 13.0 | 8.30 | 6.71 |
| Max | 150 | 71.5 | 17.5 | 106 | 39.1 | 17.7 |
| 25% | 31.0 | 20.0 | — | 32.5 | 19.7 | — |
| 75% | 110 | 54.8 | — | 75.0 | 36.2 | — |

This reduction in ammonia exposure among UCD patients reflects better overnight control among subjects receiving HPN-100, as summarized in the table below and in FIG. 11. This study shows that both AUC and Cmax for ammonia were lower with HPN-100, indicating less total ammonia exposure, and especially at night, HPN-100 exhibited a significantly stronger effect. While not statistically significant due to the small population size, this demonstrates that HPN-100 is at least as effective, and apparently more so, than PBA on an equimolar basis based on the key measure, its ability to mobilize ammonia for urinary elimination. Based on preliminary results, HPN-100 also provides more stable ammonia levels, and reduces risk of hyperammonemia. In this trial, 9 of 10 subjects who experienced both HPN-100 and sodium PBA indicated a preference for HPN-100.

In addition, in this trial, no serious adverse effects (SAEs) were observed in patients taking HPN-100, while two subjects receiving PBA experienced symptomatic hyperammonemia; and the total number of adverse effects (AEs) reported among subjects taking HPN-100 (5 subjects reported a total of 15 AEs) was lower than the number of AEs among subjects taking PBA (7 subjects reported 21 AEs).

The following table summarizes overall comparative data for sodium PBA and HPN-100, administered at equimolar rates (n=10) (see tables above and FIGS. 10-13 for additional detail).

| Parameter | Sodium PBA | HPN-100 |
|---|---|---|
| $NH_3$: Total AUC | 38.4 ± 19.6 | 26.1 ± 10.3 |
| $NH_3$ Cmax | 79.1 ± 40.1 | 56.3 ± 27.9 |
| $NH_3$ exposure: DAY (hours 6-12) | 37.1 | 32.9 |
| $NH_3$ exposure: NIGHT (hours 12-24) | 36.3 | 21.3 |
| Adverse effects | 21 reported by 7 subjects | 15 reported by 5 subjects |
| Serious adverse effects | 2 (symptomatic hyperammonemia) | 0 |
| PAGN excretion | Comparable | Comparable |

While the differences between sodium PBA and HPN-100 did not reach statistical significance due to the small sample size, HPN-100 exhibited a clear trend toward being more efficacious at equimolar dosages, and it was particularly effective for improving overnight control of ammonia levels.

Figure 9B:
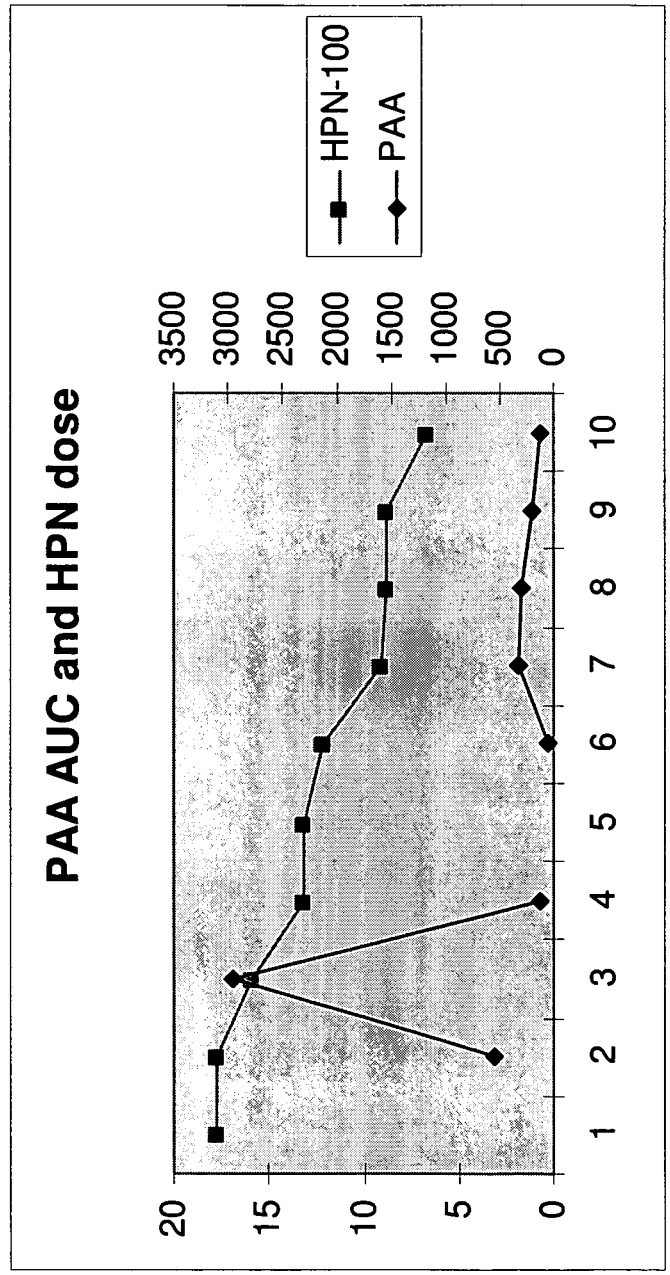
Figure 9C:
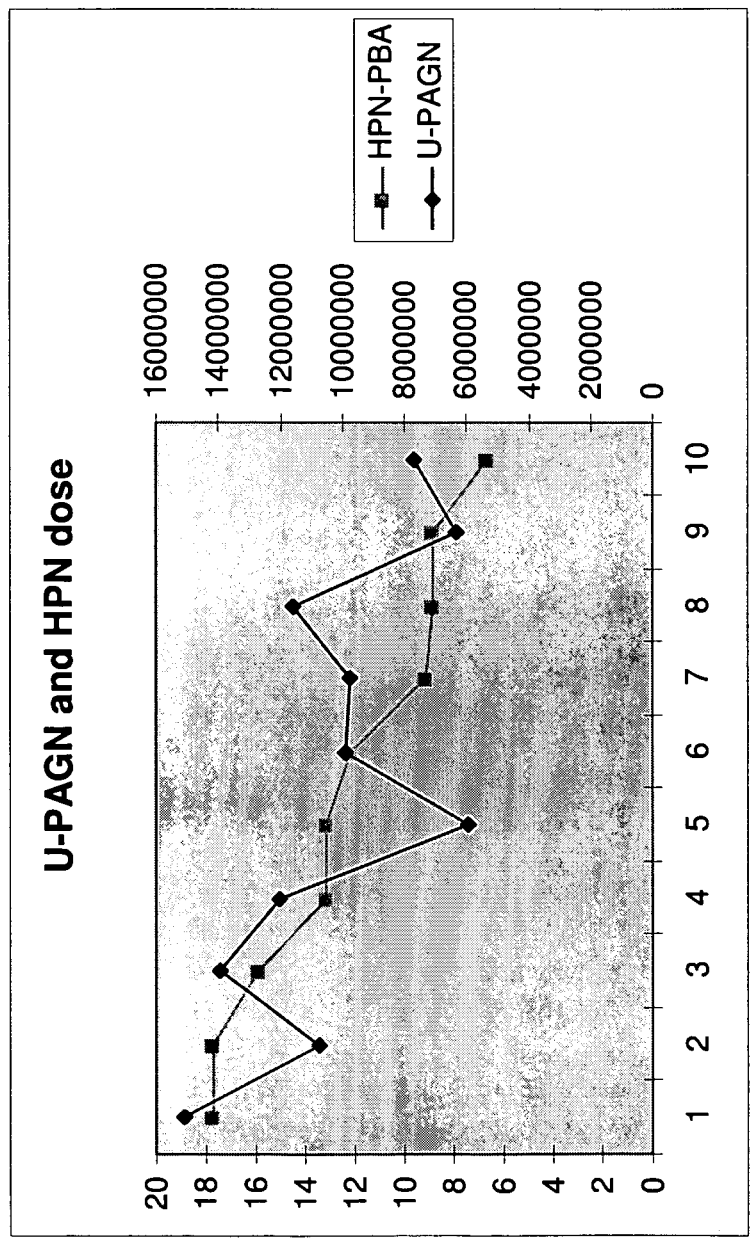

FIG. 9*a* demonstrates that PBA levels in the blood are not correlated with HPN-100 dosages received. It plots the 24-hour AUC for PBA and the Cmax for PBA against HPN-100 dosage (top panel), and while the AUC and Cmax track together in each patient, they show no relationship to HPN-100 dose: both the highest and the lowest PBA exposures occurred in patients receiving high doses of HPN-100. FIG. 9*b* shows that levels of PAA are similarly uncorrelated with HPN dosages.

FIG. 10 illustrates the trend shown in the clinical testing, where HPN-100 provided better overall control of waste nitrogen.

Figure 11:
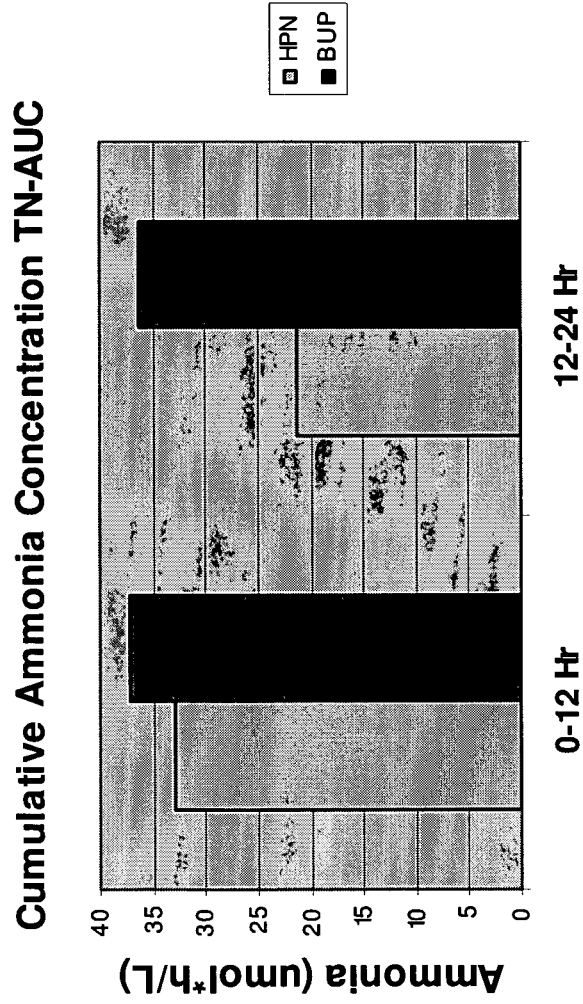
FIG. 11 shows that HPN-100 did a better job than PBA of managing plasma levels of nitrogen overnight.

FIG. 11 illustrates that improved night time control of excess ammonia is achieved with HPN-100.

FIG. 12 shows that especially for patients with higher ammonia levels when treated with sodium PBA (Na PBA), HPN-100 provides better control than sodium PBA, while in patients with lower ammonia levels (ones for whom sodium PBA seems to work relatively well), HPN-100 provides at least comparable ammonia control. Note that for patients having ammonia levels above about 40 µmol/L when treated with sodium PBA, HPN-100 at equimolar dosages provided superior control of ammonia, and consistently reduced ammonia levels to below about 40 µmol/L. Thus for patients whose ammonia levels are abnormal (e.g. above about 40 µmol/L) when treated with sodium PBA, it is expected that better ammonia control can be achieved with an equimolar amount of HPN-100. Based on this, dosages of HPN-100 can be determined as set forth herein. FIG. 13 illustrates that ammonia levels were better controlled in this test by HPN-100 than with sodium PBA, e.g., the average ammonia levels are lower, and tend to be below the upper limit for normal.

Example 4

Relationship Between Ammonia Control and Urinary PAGN Excretion

Figure 5:
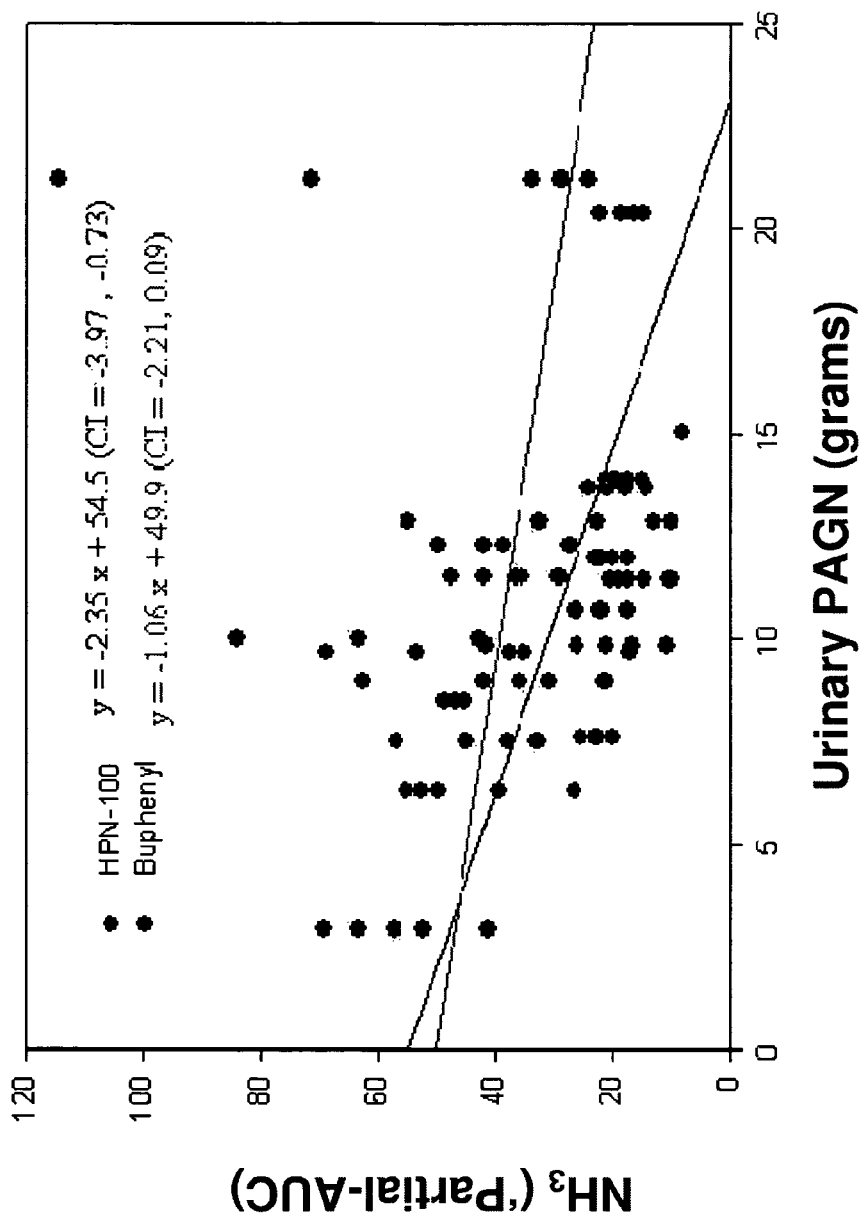
FIG. 5 presents data on ammonia levels from the tests in Example 3.

As part of the clinical study in UCD patients described in the example above (Example 3), the relationship between plasma ammonia levels and urinary excretion of PAGN was examined. Unlike blood levels of PAA or PBA which exhibited no consistent relationship to ammonia levels (i.e. ammonia control), blood ammonia assessed as the time-normalized area under the curve exhibited an inverse curvilinear relationship to urinary PAGN. That is, plasma ammonia decreased as urinary PAGN increased. Moreover, the relationship between ammonia and urinary PAGN excretion did not differ between sodium PBA and HPN-100 suggesting that this method of dose determination is independent of product formulation. FIG. 5 shows a plot of Plasma Ammonia (TN-AUC) versus Urinary PAGN Excretion.

Example 5

Experimentation with Dosing Schedule

The results of single dose PK/PD modeling observed in the examples above suggested that HPN-100 exhibits delayed release characteristics as compared with sodium PBA with a corresponding potential for increased flexibility in dosing, which was further explored in additional clinical studies described above. In one of these, HPN-100 was administered twice daily as well as in the fasted and fed state. In the other, HPN-100 was administered three times daily with meals. Both 3× daily and 2× daily dosing resulted in a similar proportion of PAGN excreted in the urine and, as demonstrated in adult UCD patients, three times daily dosing was associated with effective ammonia control.

In Example 2, a number of secondary statistical analyses comparing PK variables after fed versus fasted HPN-100 dosing and single versus multiple HPN-100 dosing were also done. There were no PK or PD differences observed when HPN-100 was administered after fasting (day 1) or with a meal (day 8). Accordingly, it is believed that HPN-100 can be effectively administered without the need for it to accompany a meal, while the label and package insert for sodium PBA (sodium PBA) indicate that it should be taken with meals. In addition to the lack of difference for PAA PK variables between the fasted and fed states (Days 8 vs 1), the table below also illustrates plasma accumulation of PAA that occurs with multiple dosing (Days 15 vs. 8).

| PK variable | Plasma PK Variables For PAA | | | |
|---|---|---|---|---|
| | Child-Pugh A (n = 8) | Child-Pugh B (n = 8) | Child-Pugh C (n = 8) | Healthy volunteers (n = 8) |
| $AUC_{0-12}$ [(µg/mL) · h] | | | | |
| Day 1 | | | | |
| Geo. mean (range) | 37.33 (7.29-78.42) | 72.20 (23.38-174.73) | 48.59 (4.75-312.43) | 50.63 (14.27-150.00) |
| CV % | 53.41 | 64.91 | 109.58 | 79.59 |
| Day 8 | | | | |
| Geo. mean (range) | 39.64 (5.96-153.14) | 73.44 (26.83-279.48) | 86.36 (28.12-367.70) | 34.07 (5.27-134.99) |
| CV % | 78.73 | 85.58 | 92.85 | 80.59 |
| Day 15 | | | | |
| Geo. mean (range) | 117.89 (23.28-413.43) | 138.95 (40.21-652.99) | 184.26 (14.97-2245.51) | 99.16 (30.06-394.79) |
| CV % | 76.82 | 99.48 | 170.56 | 88.59 |
| $AUC_{0-\tau}$ [(µg/mL) · h] | | | | |
| Day1 | | | | |
| Geo. Mean (range) | 37.33 (7.29-78.42) | 72.20 (23.38-174.73) | 48.59 (4.75-312.43) | 50.63 (14.27-150.00) |
| CV % | 53.41 | 64.91 | 109.58 | 79.59 |
| Day 15* | | | | |
| Geo. Mean (range) | 121.57 (23.28-528.73) | 153.00 (40.21-938.85) | 194.17 (14.97-3415.51) | 99.94 (30.06-420.32) |
| CV % | 92.27 | 118.54 | 198.42 | 93.08 |
| $C_{max}$ [µg/mL] | | | | |
| Day 1 | | | | |
| Geo. mean (range) | 9.65 (2.58-26.93) | 13.52 (6.94-27.97) | 10.95 (2.68-40.30) | 11.81 (4.14-29.79) |
| CV % | 63.78 | 57.70 | 82.65 | 68.72 |
| Day 8 | | | | |
| Geo. mean (range) | 10.21 (1.64-25.66) | 14.78 (4.46-42.02) | 16.03 (6.49-48.07) | 10.03 (2.90-28.43) |
| CV % | 62.25 | 74.53 | 72.29 | 66.97 |
| Day 15† | | | | |
| Geo. mean (range) | 29.07 (7.29-53.48) | 25.46 (10.54-65.40) | 33.28 (5.03-208.80) | 21.92 (7.76-61.31) |
| CV % | 44.21 | 64.26 | 121.51 | 62.88 |
| $t_{1/2}$ [h]‡ | | | | |
| Day 1 | | | | |
| Mean (SD) | 0 | 0 | 2.10 (0.32) | 0 |
| Range | | | 1.88-2.33 | |

-continued

| | Plasma PK Variables For PAA | | | |
|---|---|---|---|---|
| PK variable | Child-Pugh A (n = 8) | Child-Pugh B (n = 8) | Child-Pugh C (n = 8) | Healthy volunteers (n = 8) |
| Day 15 | | | | |
| Mean (SD) | 1.80 (0.94) | 2.76 (1.53) | 7.70 | 1.91 (0.37) |
| Range | 1.01-3.14 | 1.68-3.84 | 7.70-7.70 | 1.68-2.33 |
| $T_{max}$ [h] | | | | |
| Day 1 | | | | |
| Median (range) | 3.50 (2.00-6.00) | 5.00 (3.00-8.00) | 5.00 (2.00-8.00) | 6.00 (4.00-6.00) |
| Day 8 | | | | |
| Median (range) | 4.00 (2.00-6.00) | 5.00 (3.00-8.00) | 5.00 (4.00-8.00) | 4.00 (3.00-6.00) |
| Day 15 | | | | |
| Median (range) | 4.00 (2.00-6.00) | 4.00 (3.00-8.00) | 5.00 (0.00-8.00) | 4.00 (3.00-4.00) |

*p = 0.64 for group effect;
†p = 0.72 for group effect
‡On day 1, n = 2 in Child-Pugh group B and n = 0 in all other groups; on day 15, n = 4 in group A, 2 in group B, 1 in group C, and 3 in group D
$AUC_{0-12}$, area under the plasma concentration curve from time 0 up to 12 hours after dosing;
$AUC_{0-t}$, area under the plasma concentration curve from time 0 to the last measurable concentration;
$C_{max}$, maximum observed plasma concentration;
CV, coefficient of variation;
geo. Mean, geometric mean;
n, number of subjects;
SD, standard deviation;
$T_{max}$, time to maximum observed plasma concentration;
$t_{1/2}$, half-life Example 6

PK/PD Modeling Results

In the case of most drugs, the fraction of an orally administered dose which is removed and metabolized by the liver prior to reaching the systemic circulation (i.e. first pass effect) is not considered bioavailable, since it does not enter the systemic circulation and therefore is not able to reach its target organ or receptor. However, this is not the case for ammonia scavenging drugs described in this invention. Since hepatocytes and possibly enterocytes contain the enzymes necessary for conversion of PBA to PAA and conversion of PAA to PAGN and since glutamine is present in the splanchnic as well as the systemic circulation, it is likely that PBA can be converted to PAGN prior to reaching the systemic circulation (i.e. "pre-systemically") and that this PBA is fully effective with respect to ammonia scavenging (FIG. 6); i.e. fully active. To verify this possibility, PK/PD modeling using NONMEM VI (Icon, Ellicot City, Md.) was carried out on plasma and urinary metabolite data (over 5000 data points) from the clinical studies described above involving healthy adults, subjects with cirrhosis and UCD subjects. The results of this PK/PD modeling have validated the model depicted in FIG. 3. Moreover, the modeling has verified that HPN-100 exhibits slow release characteristics as compared with sodium PBA and provided an explanation for the poor correlation between blood levels of PBA/PAA and ammonia and the importance of urinary PAGN is dose adjustment. Key conclusions resulting from the PK/PD modeling were as follows 1. PBA is more slowly absorbed (~40% as fast) from the intestine after administration of HPN-100 versus sodium PBA (absorption rate constants and absorption half-lives for HPN-100 and sodium PBA are 0.544 $h^{-1}$ vs. 1.34 $h^{-1}$ and 1.27 h vs. 0.52 h, respectively).
2. The lower plasma levels of PBA following administration of HPN-100, as compared with sodium PBA, reflect results indicating a fractionally greater amount of PBA (31% vs. 1%) being converted pre-systemically (to PAA and PAGN) following administration of HPN-100 than Na PBA.
3. In a dataset containing healthy, cirrhotic, and UCD individuals, diagnosis was introduced as a covariate on the estimated bioavailability of HPN-100 revealing a 32% lower estimated bioavailability of PBA in healthy adults compared to adult UCD patients. Cirrhotic and UCD patients had similar PBA bioavailability following HPN-100 treatment.

Example 7

ADME Study In Three Cynomolgous Monkeys

To assess the preclinical handling of ammonia scavenging drugs, 600 mg/kg of either radio labeled sodium PBA or radio labeled HPN-100 was administered as a single dose to 3 cynomolgous monkeys. These monkeys were chosen because, like humans (and unlike most other species), they metabolize PAA to PAGN and thus provide a useful model for testing prodrugs of PAA. This study corroborated clinical findings summarized in Examples 1-3, including the following: (a) dosing with oral sodium PBA or oral HPN-100 did not result in 100% conversion to urinary PAGN, (b) plasma PBA and PAA blood levels did not correlate consistently with ammonia scavenging activity as reflected by urinary PAGN output, and (c) HPN-100 exhibited slow release characteristics as compared with sodium PBA.

Radio labeled PBA and PAA entered the systemic circulation rather slowly following administration of radio labeled HPN-100 [Cmax for PBA was achieved 1.5 hours post-dosing (52.2 μg/mL) and Cmax for PAA was achieved 8 hours post dosing (114 μg/mL)], corroborating the findings observed in humans (including the PK/PD modeling), and essentially no HPN-100 appeared in systemic circulation or in excretions. About 90% of radioactive material derived from HPN-100 that was excreted in urine was PAGN, accounting for 39% of the administered HPN-100. By contrast, when oral sodium PBA was administered, PAGN accounted for only 23% of the radio labeled material, and unchanged PBA accounted for 48% of the administered dosage of oral sodium PBA. Thus oral sodium PBA was utilized less efficiently than HPN-100, and an unexpectedly high amount of PBA was excreted unchanged.

Example 8

Biological and Anatomical Considerations

Unlike most drugs which act on a target organ/cell/receptor (etc.) perfused by systemic blood, ammonia scavenging drugs of the types covered by this invention do not act on a target organ, rather they act through the combination of PAA with glutamine to form PAGN (FIG. 6). Since glutamine is present in the splanchnic as well as the systemic circulation and since the liver is a metabolically active organ capable of catalyzing all steps involved in the conversion of HPN-100 or PBA to PAA and then to PAGN, the data accumulated to date, including the PK/PD modeling, as well as anatomical consideration lead us to the conclusion that the formation of PAGN from PBA/PAA occurs to a significant degree before PBA/PAA reach the systemic circulation (e.g. within the liver). This is especially true when HPN-100 is administered as a PBA prodrug. This explains the poor correlation between plasma levels and ammonia trapping effects and leads to the conclusion that the dosing and dose adjustment of these PBA prodrugs should be based on urinary excretion of PAGN and total urinary nitrogen. FIG. 6 illustrates how this occurs.

For certain clinical trials, particularly for comparing HPN-100 to PBA, HPN-100 will be administered at a dose that is equivalent (equimolar) to an amount of sodium PBA that would be considered suitable for the particular patient; and the dosage can then be adjusted by the methods described herein. For example, the HPN-100 dose range will match the PBA molar equivalent of the approved sodium PBA (sodium phenylbutyrate) (NaPBA) dose range. HPN-100 will be administered three times a day (TID) with meals. Note that the conversion of the dose of NaPBA to the dose of HPN-100 involves correction for their different chemical forms (i.e. HPN-100 consists of glycerol in ester linkage with 3 molecules of PBA and contains no sodium) (NaPBA [g]× 0.95=HPN-100 [g]) as well as correction for the specific gravity of HPN-100, which is 1.1 g/mL.

| HPN-100 Dose Ranges Corresponding to Recommended Daily Doses of Sodium PBA | | |
|---|---|---|
| Sodium PBA | HPN-100 PBA Equivalent Dose (mg) | HPN-100 PBA Equivalent Dose (mL) |
| 450-600 mg/kg/day (patients ≤ 20 kg) | 428-570 mg/kg/day | 0.39-0.52 mL/kg/day |
| 9.9-13.0 g/m2/day (patients > 20 kg) | 9.4-12.4 g/m2/day | 8.6-11.2 mL/m2/day |
| Maximum Daily Dose: 20 g | Maximum Daily Dose: 19 g | 17.4 mL |

[1]20 g of sodium PBA contains ~17.6 g of phenylbutyric acid; 19 g of HPN-100 contains ~17.6 g of phenylbutyric acid

Example 9

Determination of a Starting Dosage and Dose Adjustment of HPN-100

A patient having a nitrogen retention state (e.g. an inherited urea cycle disorder or cirrhosis) who is currently not being treated with an ammonia scavenging agent as described in this invention is determined clinically to be in need of such treatment. This clinical determination would be based upon a variety of factors (e.g. signs and symptoms of HE in patients with cirrhosis, elevated blood ammonia levels).

The starting dosage is based on clinical considerations, including the estimation of residual urea synthetic capacity (an infant with UCD presenting with hyperammonia in the first few days of life would be presumed to have no significant urea synthesis capacity) and appropriate dietary protein intake (i.e., infants with UCD require increased dietary protein to support body growth, but long-term dietary protein restriction in patients with cirrhosis is usually ineffective or counterproductive, and the methodology outlined in this invention. For example, an adult with limited residual urea synthetic capacity is treated with an initial dosage of HPN-100 of 19 g per day and placed on a protein-limited diet containing about 25 g of protein per day. The patient's daily urinary output of PAGN is monitored. The daily intake of HPN-100 amounts to 19 g of HPN-100, at a molecular weight of ~530, which is 0.0358 mol HPN-100. Each mole of HPN-100 can theoretically be converted into three moles of PAA and thus three moles of PAGN, so the 19 g daily dosage of HPN-100 could produce 0.108 mol of PAGN in vivo. If entirely converted into PAGN and all of the PAGN is excreted in the urine, the theoretical quantity of PAGN would be 28.4 g per day, which would be sufficient to mediate the waste nitrogen excretion resulting from ~41 grams of dietary protein, assuming that 16% of dietary protein is nitrogen and ~47% of dietary nitrogen is excreted as waste nitrogen (see Brusilow).

However, as demonstrated herein, HPN-100 is typically converted into urinary PAGN with an efficiency of about 60% to 75% (typically about 60% conversion was found in UCD patients; conversion in cirrhotic patients was about 75%), thus the physician would expect to observe about 17 g of urinary PAGN output per day from this dosage of HPN-100. This corresponds to ~25 grams of dietary protein—which is similar to the prescribed amount, but less than the theoretical amount (41 grams) this dosage of HPN-100 might have been expected to account for theoretically. Thus the adjustment for 60-75% efficiency significantly affects the overall treatment program, and knowing what efficiency to expect enables the treating physician to avoid putting the patient on a diet containing too much protein for the patient to manage on this dosage of HPN-100.

When monitoring the patient, if the doctor observes a higher output of urinary PAGN than expected, the dosage of HPN-100 is reduced proportionally; thus if 21 g of urinary PAGN per day is observed, the physician will reduce the dosage of HPN-100 to (17/21)*19 g=15 g. Similarly, if urinary PAGN output is below that expected amount, such as 12 g per day, the amount of HPN-100 would be increased: if 12 g is observed and 17 is expected, the physician could adjust the HPN-100 dosage to (17/12)*19 g=27 g HPN-100 per day, if that dosage is within a range considered safe to administer to the patient. Either the dosage of HPN-100 or dietary protein intake could be adjusted to optimize the treatment plan for this subject.

Optionally, the urinary PAGN output may be determined as a ratio of urinary PAGN concentration to urinary creatinine concentration; creatinine levels are typically stable enough for a given individual to provide a normalization factor for urine volume so that rather than determining total daily urinary PAGN, the physician can estimate total daily urinary PAGN from testing a single urine sample.

The physician may also monitor the plasma ammonia levels and dietary protein intake in the patient to ascertain whether the patient's dietary protein intake and drug treatment combined are producing the appropriate therapeutic effect. Dietary protein intake or drug dosage or both could be adjusted to attain a normal or desired plasma ammonia level, e.g., a level below about 40 umol/L. However, as demonstrated by the observations described herein, the physician would not use plasma levels of PAA or PBA to adjust the dosage of HPN-100 or otherwise guide treatment, as those levels do not correlate well with the ammonia scavenging effect of the administered HPN-100.

If the 19 g dose of HPN-100 is determined to be inadequate (e.g. patient requires an increase in dietary protein which would result in excretion of waste nitrogen exceeding his or her urea synthesis capacity and PAGN excretion), HPN-100 dose would be increased sufficiently to cover the necessary dietary protein and the same methodology of dose adjustment based on urinary PAGN excretion would be applied to determine that dosage of HPN-100.

In a subject having little or no urea synthesis capacity where essentially all urinary nitrogen would be accounted for by PAGN, the ammonia scavenging effect may be monitored by determination of total urinary nitrogen (TUN), rather than directly measuring PAGN levels in the urine.

Optionally, the TUN can be used as a measure of urea synthesis capacity, by subtracting the amount of nitrogen present as PAGN.

Example 10

Determination of a Dosage of HPN-100 for a Patient Already on Sodium PBA

A patient with a UCD already on sodium PBA who is to be transitioned to HPN-100 would undergo assessment of dietary protein and measurement of urinary PAGN excretion.

If the patient is judged to be adequately controlled on sodium PBA, then the starting dose of HPN-100 would be the amount necessary to deliver the same amount of PAA (e.g. 19 grams of HPN-100 would correspond to 20 grams of sodium PBA). Subsequent dose adjustment would be based on repeated measurement of urinary PAGN as well as assessment of dietary protein and ammonia. However, as demonstrated by the observations described herein, the physician would not use plasma levels of PAA or PBA either to determine the initial dosage of HPN-100 or adjust the dosage of HPN-100 or otherwise guide treatment, as those levels do not correlate well with the ammonia scavenging effect of the administered HPN-100.

If the patient is determined to be inadequately controlled on sodium PBA, then the starting dose of HPN-100 would be selected to deliver an amount of PAA higher than the dose of sodium PBA provided such HPN-100 dosage is otherwise appropriate. Subsequent dose adjustment would be based on repeated measurement of urinary PAGN as well as assessment of dietary protein and plasma ammonia. However, as demonstrated by the observations described herein, the physician would not use plasma levels of PAA or PBA either to determine the initial dosage of HPN-100 or adjust the dosage of HPN-100 or otherwise guide treatment, as those levels do not correlate well with the ammonia scavenging effect of the administered HPN-100.

Optionally, for example in a 'fragile' UCD patient with a history of repeated episodes of hyperammonemia, the conversion from sodium PBA to HPN-100 might occur in more than one step, whereby, at each step, the dose of sodium PBA would be reduced in an amount corresponding to the amount of PAA delivered by the incremental dose of HPN-100.

If the dose of HPN-100 is determined to be inadequate (e.g. patient requires an increase in dietary protein which would result in production of waste nitrogen exceeding his or her urea synthesis capacity and PAGN excretion), HPN-100 dose would be increased sufficiently to cover the necessary dietary protein and the same methodology of dose adjustment based on urinary PAGN excretion would be applied.

The examples set forth herein are illustrative only, and should not be viewed as limiting the invention.

The invention claimed is:

1. A method of treating a patient having a urea cycle disorder comprising (a) determining a target urinary phenylacetyl glutamine (PAGN) output (b) calculating an effective initial dosage of a phenylacetic acid (PAA) prodrug selected from glyceryl tri-[4-phenylbutyrate] (HPN-100) and phenylbutyric acid (PBA) or a pharmaceutically acceptable salt of PBA, wherein the effective dosage of PAA prodrug is calculated based on a mean conversion of PAA prodrug to urinary PAGN of about 60%; and (c) administering the effective initial dosage of PAA prodrug to the patient.

2. The method of claim 1, wherein target urinary PAGN output is determined as a ratio of the concentration of urinary PAGN to urinary creatinine.

3. The method of claim 1, wherein administration of the effective initial dosage of PAA prodrug produces a normal plasma ammonia level in the patient.

4. The method of claim 1, wherein the target PAGN output takes into account the patient's dietary protein intake.

5. The method of claim 1, wherein the target PAGN output takes into account the patient's residual urea synthesis capacity.

6. The method of claim 1, wherein the PAA prodrug is HPN-100.

7. The method of claim 1, wherein the pharmaceutically acceptable salt of PBA is sodium PBA.

8. A method of administering a phenylacetic acid (PAA) prodrug selected from glyceryl tri-[4-phenylbutyrate] (HPN-100) and phenylbutyric acid (PBA) or a pharmaceutically acceptable salt of PBA to a patient having a from urea cycle disorder comprising (a) administering a first dosage of the PAA prodrug; (b) determining urinary phenylacetyl glutamine (PAGN) excretion following administration of the first dosage of the PAA prodrug; (c) determining an effective dosage of the PAA prodrug based on the urinary PAGN excretion, wherein the effective dosage is based on a mean conversion of PAA prodrug to urinary PAGN of about 60%; and (d) administering the effective dosage to the patient.

9. The method of claim 8, wherein urinary PAGN excretion is determined as a ratio of the concentration of urinary PAGN to urinary creatinine.

10. The method of claim 8, wherein the pharmaceutically acceptable salt of PBA is sodium PBA.

11. The method of claim 8, wherein the PAA prodrug is HPN-100.

12. The method of claim 8, wherein administration of the effective dosage of PAA prodrug produces a normal plasma ammonia level in the patient.

* * * * *

UNITED STATES PATENT AND TRADEMARK OFFICE
CERTIFICATE OF CORRECTION

PATENT NO. : 8,642,012 B2  
APPLICATION NO. : 12/350111  
DATED : February 4, 2014  
INVENTOR(S) : Bruce Scharschmidt Page 1 of 1

It is certified that error appears in the above-identified patent and that said Letters Patent is hereby corrected as shown below:

In the Claims

Column 42, line 44, claim 8, remove "from" between "having a" and "urea".

Signed and Sealed this
Twenty-fourth Day of June, 2014

Michelle K. Lee
*Deputy Director of the United States Patent and Trademark Office*